US007750016B2

(12) United States Patent  
Goldstein

(10) Patent No.: US 7,750,016 B2  
(45) Date of Patent: Jul. 6, 2010

(54) HYDROXYALKYL SUBSTITUTED PYRIDO-7-PYRIMIDIN-7-ONES

(75) Inventor: David Michael Goldstein, San Jose, CA (US)

(73) Assignee: Roche Palo Alto LLC, Palo Alto, CA (US)

(*) Notice: Subject to any disclaimer, the term of this patent is extended or adjusted under 35 U.S.C. 154(b) by 0 days.

(21) Appl. No.: 11/985,821

(22) Filed: Nov. 19, 2007

(65) Prior Publication Data

US 2008/0119497 A1    May 22, 2008

Related U.S. Application Data

(63) Continuation of application No. 10/987,656, filed on Nov. 12, 2004, now Pat. No. 7,348,331.

(60) Provisional application No. 60/519,789, filed on Nov. 13, 2003.

(51) Int. Cl.
    C07D 471/04    (2006.01)
    A61K 31/519   (2006.01)
    A61P 29/00    (2006.01)
    A61P 1/00     (2006.01)
    A61P 11/06    (2006.01)
    A61P 21/00    (2006.01)

(52) U.S. Cl. .................. 514/264.11; 544/279

(58) Field of Classification Search ............ 514/264.11; 544/279
    See application file for complete search history.

(56) References Cited

U.S. PATENT DOCUMENTS

| 4,215,216 | A | 7/1980 | Scotese et al. |
| 5,037,826 | A | 8/1991 | Blythin et al. |
| 5,620,981 | A | 4/1997 | Blankley et al. |
| 5,733,913 | A | 3/1998 | Blankley et al. |
| 5,733,914 | A | 3/1998 | Blankley et al. |
| 5,945,422 | A | 8/1999 | Doherty et al. |
| 6,518,276 | B2 | 2/2003 | Arzeno et al. |
| 6,696,566 | B2 * | 2/2004 | Chen et al. ................. 544/261 |
| 6,936,612 | B2 * | 8/2005 | Barvian et al. ......... 514/252.16 |
| 2003/0073668 | A1 | 4/2003 | Booth et al. |
| 2003/0149001 | A1 | 8/2003 | Barvian et al. |

FOREIGN PATENT DOCUMENTS

| EP | 0 278 686 A1 | 8/1988 |
| WO | WO 93/17682 A1 | 9/1993 |
| WO | WO 96-34867 A1 | 11/1996 |
| WO | WO 98/33798 A2 | 8/1998 |
| WO | WO 99/61444 A2 | 12/1999 |
| WO | 0 790 997 B1 | 3/2000 |
| WO | WO 01/55148 A1 | 8/2001 |
| WO | WO 01/70741 A1 | 9/2001 |
| WO | WO 02/64594 * | 2/2002 |
| WO | WO03/062236 * | 1/2003 |

OTHER PUBLICATIONS

Feldmann, Nature Immunology, vol. 2, No. 9, Sep. 2001, pp. 771-773.*
Johnson, et al., Science, vol. 298, Dec. 6, 2002, 1911-1912.*
Westra, et al., Ann. Rheum. Dis. 2004;63:1453-1459.*
Seto, et al., J Clin Invest. 2004, 113(5): 718-726.*
Liu-Bryan, et al., Joint Bone Spine, vol. 72, #4, Jul. 2005, 295-302.*
Boschelli, et al, "Synthesis and Tyrosine Kinase Inhibitory Activity of a Series of 2-Amino-8H-pyrido[2,3-d]pyrimidines. Identification of Potent, Selective Platelet-Derived Growth Factor Receptor Tyrosine Kinase Inhibitors," Journal of Med. Chem., (1998), pp. 4365-4377, vol. 41.
Klutchko, et al., "2-Substituted Aminopyrido[2,3-d] pyrimidin-7(8H)-ones. Structure-Activity Relationships Against Selected Tyrosine Kinases and in Vitro and in Vivo Anticancer Activity," Journal of Med. Chem., (1998), pp. 3276-3292, vol. 41.
Barvian, et al., "Pyrido[2,3-d]pyrimidin-7-one Inhibitors of Cyclin-Dependent Kinases," Journal of Med. Chem., (2000), pp. 4606-4616, vol. 43.
Hamby, et al., "Structure-Activity Relationships for a Novel Series of Pyrido[2,3-d]pyrimidine Tyrosine Kinase Inhibitors," Journal Med. Chem., (1997), pp. 2296-2303, vol. 40.
Edwards, et al., "Osmotic stress induces both secretion and apoptosis in rat alveolar type ii cells," APStracts 5:0150L, Jun. 16, 1998.
Munoz et al., "Causes of Alzheimer's Disease," CMAJ (Canadian Medical Assoc.), (2000), pp. 65-72, vol. 162(1).
Palmer, "Pharmacotherapy for Alzheimer's disease: progress and prospects," TRENDS in Pharmacological Sciences, Sep. 2002, pp. 426-433, vol. 23(9).

(Continued)

Primary Examiner—James O Wilson
Assistant Examiner—Cecilia M Jaisle
(74) Attorney, Agent, or Firm—Robert C. Hall

(57) ABSTRACT

Compounds of the Formula:

where $X^1$, $Ar^1$, $R^1$, and $R^2$ are as defined herein, and compositions comprising the same. Also provided are methods for using compounds of Formula I in treating p38 mediated disorders in a patient.

17 Claims, No Drawings

OTHER PUBLICATIONS

Boehm et al., *Expert Opinion on Therapeutic Patents*, "New inhibitors of p38 kinase," (2000), pp. 25-37, vol. 10(1), Ashley Publications Ltd., ISSN 1354-3776.

Dalrymple et al., "p38 Mitogen Activated Protein Kinase as a Therapeutic Target for Alzheimer's Disease," *J. Molecular Neuroscience*, (2002), vol. 19, pp. 295-299.

Haddad et al., "Role of P38Map Kinase in LPS-Induced Airway Inflammation in the Rat," *Brit. J. Pharmacology*, (2001), pp. 1715-1724, vol. 132(8).

Underwood et al., "SB 239063, a p38 MAPK inhibitor, reduces neutrophilia, inflammatory cytokines, MMP-9, and fibrosis in lung," *Am. J. Physiol. Lung Cell Mol. Physiol.*, (2000), pp. L895-L902, vol. 279.

Lee et al., "Review, Inhibition of p38MAP kinase as a therapeutic strategy", *Immunopharmacology*, (2000), pp. 185-201, vol. 47.

\* cited by examiner

HYDROXYALKYL SUBSTITUTED PYRIDO-7-PYRIMIDIN-7-ONES

CROSS REFERENCE TO RELATED APPLICATIONS

This Application is a continuation of U.S. patent application Ser. No. 10/987,656 filed on Nov. 12, 2004, now U.S. Pat. No. 7,348,331, which claims the benefit under Title 35 U.S.C. 119(e) of U.S. Provisional Application No. 60/519,789 filed Nov. 13, 2003. The disclosures of the aforementioned applications are incorporated herein by reference in their entirety.

FIELD OF THE INVENTION

The present invention relates to pyridopyrimidines and derivatives thereof. In particular, the present invention provides 2,6-disubstituted 7-oxo-pyrido[2,3-d]pyrimidines, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents,* 2000, 10(1).

The inhibition of these cytokines by inhibition of the p38 kinase is of benefit in controlling, reducing and alleviating many of these disease states.

Certain 6-aryl-pyrido[2,3-d]pyrimidin-7-ones, -7-imines and 7-thiones are disclosed as inhibitors of protein tyrosine kinase mediated cellular proliferation in WO 96/34867, published Nov. 7, 1996 (Warner Lambert). Other 6-aryl-pyrido[2,3-d]pyrimidines and naphthyridines are also disclosed as inhibitors of tyrosine kinase in WO 96/15128, published May 23, 1996 (Warner Lambert). 6-alkyl-pyrido[2,3-d]pyrimidin-7-ones are disclosed as inhibitors of cyclin-dependent kinases in WO 98/33798, published Aug. 6, 1998 (Warner Lambert). Certain 4-amino-pyridopyrimidines are disclosed as inhibitors of dihydrofolate reductase in EP 0 278 686A1, published Aug. 8, 1988 (Wellcome Foundation).

SUMMARY OF THE INVENTION

One aspect of the present invention provides compounds of the formula:

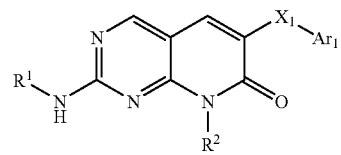

where
 $X^1$ is O, S(O)$_n$ (where n is 0, 1 or 2), or C=O;
 $Ar^1$ is aryl or heteroaryl;
 $R^1$ is alkoxyalkyl, alkyl, cycloalkyl, cycloalkylalkyl, heterocyclyl, hydroxyalkyl, or hydroxycycloalkyl; and
 $R^2$ is hydroxyalkyl, oxoalkyl or hydroxycycloalkyl.

Another aspect of the present invention provides a pharmaceutical formulation comprising a Compound of Formula I and a pharmaceutically acceptable carrier, diluent, or excipient therefor.

While certain substituted pyrido-7-pyrimidin-7-ones are known to be active in an enzymatic in vitro assay against p38 (see for example, commonly assigned U.S. patent application Ser. No. 10/073,845, filed Feb. 11, 2002, entitled "6-Substituted Pyrido-Pyrimidines", which is incorporated herein by reference in its entirety), surprisingly and unexpectedly, the present inventor has discovered that Compound of Formula I have a significantly higher activity in a lipopolysacchararide (LPS) induced human whole blood cysteine production assay than compounds that have previously been disclosed.

Compounds of Formula I are inhibitors of protein kinases, and exhibit effective activity against p38 in vivo. They are selective against p38 kinase relative to cyclin-dependent kinases and tyrosine kinases. Therefore, compounds of the present invention can be used for the treatment of diseases mediated by the pro-inflammatory cytokines such as TNF and IL-1. Thus another aspect of the present invention provides a method for treating p38 mediated diseases or conditions in which a therapeutically effective amount of a Compound of Formula I is administered to a patient.

DETAILED DESCRIPTION OF THE INVENTION

Definitions
Unless otherwise stated, the following terms used in the specification and claims have the meanings given below:
"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Aryl" means a monovalent monocyclic or bicyclic aromatic hydrocarbon radical which is optionally substituted independently with one or more substituents, preferably one, two or three, substituents preferably selected from the group consisting of alkyl, hydroxy, alkoxy, haloalkyl, haloalkoxy, halo, nitro, cyano, amino, monoalkylamio, dialkylamino, methylenedioxy, ethylenedioxy and acyl. A particularly preferred aryl substituent is halide. More specifically the term aryl includes, but is not limited to, phenyl, chlorophenyl, fluorophenyl, difluorophenyl (such as 2,4- and 2,6-difluorophenyl), methoxyphenyl, 1-naphthyl, 2-naphthyl, and the derivatives thereof.

"Cycloalkyl" refers to a saturated monovalent cyclic hydrocarbon radical of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, monoalkylamio, dialkylamino, and acyl. A particularly preferred group of cycloalkyl substituents include alkyl, hydroxy, alkoxy, haloalkyl, haloalkoxy, and halo. An especially preferred group of cycloalkyl substituents include alkyl, hydroxy, alkoxy, and halo.

"Cycloalkylalkyl" refers to a moiety of the formula $R^c$-$R^d$—, where $R^c$ is cycloalkyl and $R^d$ is alkylene as defined herein.

"Halo" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroaryl" means a monovalent monocyclic or bicyclic radical of 5 to 12 ring atoms having at least one aromatic ring containing one, two, or three ring heteroatoms selected from N, O, or S (preferably N or O), the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxy, alkoxy, halo, nitro or cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heterocyclyl" means a saturated or unsaturated non-aromatic cyclic radical of 3 to 8 ring atoms in which one or two ring atoms are heteroatoms selected from N, O, or $S(O)_n$ (where n is an integer from 0 to 2), preferably N or O, the remaining ring atoms being C, where one or two C atoms may optionally be replaced by a carbonyl group. The heterocyclyl ring may be optionally substituted independently with one, two, or three substituents selected from alkyl, haloalkyl, hydroxyalkyl, halo, nitro, cyano, cyanoalkyl, hydroxy, alkoxy, amino, monoalkylamino, dialkylamino, aralkyl, —$(X)_n$—$C(O)R^e$ (where X is O or $NR^f$, n is 0 or 1, $R^e$ is hydrogen (where X is $NR^f$), alkyl, haloalkyl, hydroxy (when n is 0), alkoxy, amino, monoalkylamino, dialkylamino, or optionally substituted phenyl, and $R^f$ is H or alkyl), alkylene-$C(O)R^g$ (where $R^g$ is alkyl, —$OR^h$ or $NR^iR^j$ and $R^h$ is hydrogen, alkyl or haloalkyl, and $R^i$ and $R^j$ are independently hydrogen or alkyl), or —$S(O)_nR^k$ (where n is an integer from 0 to 2) such that when n is 0, $R^k$ is hydrogen, alkyl, cycloalkyl, or cycloalkylalkyl, and when n is 1 or 2, $R^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, monoalkylamino, dialkylamino, aralkyl, and —$S(O)_nR^k$. In particular, the term heterocyclyl includes, but is not limited to, tetrahydrofuranyl, pyridinyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof, each of which may be optionally substituted.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to; 2-, 3-, or 4-hydroxycyclohexyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, halo, nitro, cyano, amino, methylenedioxy, ethylenedioxy, and acyl.

"Oxoalkyl" means an alkyl group which is substituted with one or more carbonyl oxygen moiety (i.e., =O), such as a moiety of the formula $R^z$—$C(=O)R^y$—, wherein $R^y$ is alkylene and $R^z$ is alkyl. Exemplary oxoalkyl groups include 2-propanon-3-yl, 2-methyl-3-butanon-4-yl, and the like.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use.

A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic-acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, N.Y.-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2 d ed. 1991) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "treating", "contacting" or "reacting" when referring to a chemical reaction, means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

Compounds of the Invention

One embodiment of the present invention provides a compound of the formula:

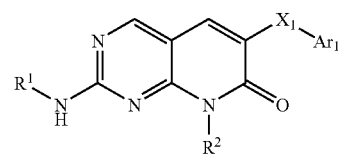

where
 $X^1$ is O, $S(O)_n$ (where n is 0, 1 or 2), or C=O;
 $Ar^1$ is aryl or heteroaryl;
 $R^1$ is alkoxyalkyl, alkyl, cycloalkyl, cycloalkylalkyl, heterocyclyl, hydroxyalkyl, or hydroxycycloalkyl; and
 $R^2$ is hydroxyalkyl, oxoalkyl pr hydroxycycloalkyl.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. In addition to the compounds described above, the compounds of the present invention include all tautomeric forms. Furthermore, the present invention also includes all pharmaceutically acceptable salts of those compounds along with prodrug forms of the compounds and all stereoisomers whether in a pure chiral form or a racemic mixture or other form of mixture.

The compounds of Formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

In one embodiment, $Ar^1$ is aryl. A particularly preferred $Ar^1$ is optionally substituted phenyl. In certain embodiments, $Ar^1$ is phenyl optionally substituted one or more times with alkyl, halo, haloalkyl or alkoxy. A more preferred $Ar^1$ is disubstituted phenyl such as 2,4-disubstituted phenyl. Still more preferably, $Ar^1$ is 2,4-dihalo substituted phenyl. An especially preferred $Ar^1$ is 2,4-difluorophenyl.

Still in another embodiment, $X^1$ is O.

In another embodiment, $R^1$ is alkoxyalkyl, alkyl, cycloalkyl, cycloalkylalkyl, hydroxyalkyl, or heterocyclyl. Within this group, a particularly preferred $R^1$ includes optionally substituted tetrahydropyranyl, 1-methyl-2-methoxyethyl, optionally substituted cyclopentyl, optionally substituted cyclopropyl, iso-propyl, optionally substituted cyclohexyl, 1-(2-hydroxyethyl)-3-hydroxypropyl, 1-hydroxymethyl-2-hydroxypropyl, 1-hydroxymethyl-3-hydroxypropyl, 1-methylpropyl, 2-hydroxy-1-methylethyl, 1-(2-methoxyethyl)-3-methoxypropyl, N-methanesulfonyl piperidinyl, ethyl, methyl, 2-hydroxypropyl, neopentyl, 1,1-dimethyl-2-hydroxyethyl, 1-(hydroxymethyl)propyl, 2-methylpropyl, cyclopropylmethyl, optionally substituted cyclobutyl, 1,2-dimethyl-2-hydroxypropyl, and 1-(hydroxymethyl)-2-hydroxyethyl.

Yet in another embodiment, a preferred $R^1$ is hydroxyalkyl, with 2-hydroxy-1-methylethyl being a particularly preferred $R^1$. Especially preferred $R^1$ includes enantiomerically enriched 2-hydroxy-1-methylethyl, i.e., (R)- and (S)-2-hydroxy-1-methylethyl.

In one specific embodiment, $R^2$ is 2-hydroxyethyl, 3-hydroxypropyl, 2-hydroxypropyl, 1-(2-hydroxyethyl)-3-hydroxypropyl, or 2-oxopropyl.

In another embodiment, $R^2$ is hydroxyalkyl. Within this group, a particularly preferred $R^2$ is 2-hydroxyethyl, 3-hydroxypropyl, 2-hydroxypropyl, and 1-(2-hydroxyethyl)-3-hydroxypropyl. An especially preferred $R^2$ is 2-hydroxypropyl.

Still further, combinations of the preferred groups described herein form other preferred embodiments. For example, in one particularly preferred embodiment $R^1$ is (R)- or (S)-2-hydroxy-1-methylethyl, $R^2$ is (R)- or (S)-2-hydroxypropyl, or 2-oxopropyl, $X^1$ is O and $Ar^1$ is 2,4-difluorophenyl.

In one embodiment the present invention provides a compound of formula I wherein $Ar^1$ is aryl and $X^1$ is O. In another embodiment the present invention provides a compound of formula I wherein $Ar^1$ is aryl, $X^1$ is O and $R^1$ is alkoxyalkyl, alkyl, cycloalkyl, cycloalkylalkyl, hydroxyalkyl, or heterocyclyl. In still another embodiment the present invention provides a compound of formula I wherein $Ar^1$ is aryl, $X^1$ is O and $R^1$ is tetrahydropyranyl, 1-methyl-2-methoxyethyl, cyclopentyl, cyclopropyl, iso-propyl, cyclohexyl, 1-(2-hydroxyethyl)-3-hydroxypropyl, 1-hydroxymethyl-2-hydroxypropyl, 1-hydroxymethyl-3-hydroxypropyl, 1-methylpropyl, 2-hydroxy-1-methylethyl, 1-(2-methoxyethyl)-3-methoxypropyl, N-methanesulfonyl piperidinyl, ethyl, methyl, 2-hydroxypropyl, neopentyl, 1,1-dimethyl-2-hydroxyethyl, 1-(hydroxymethyl)propyl, 2-methylpropyl, cyclopropylmethyl, cyclobutyl, 1,2-dimethyl-2-hydroxypropyl, or 1-(hydroxymethyl)-2-hydroxyethyl. In yet another embodiment the present invention provides a compound of formula I wherein $Ar^1$ is aryl, $X^1$ is O, $R^1$ is tetrahydropyranyl, 1-methyl-2-methoxyethyl, cyclopentyl, cyclopropyl, iso-propyl, cyclohexyl, 1-(2-hydroxyethyl)-3-hydroxypropyl, 1-hydroxymethyl-2-hydroxypropyl, 1-hydroxymethyl-3-hydroxypropyl, 1-methylpropyl, 2-hydroxy-1-methylethyl, 1-(2-methoxyethyl)-3-methoxypropyl, N-methanesulfonyl piperidinyl, ethyl, methyl, 2-hydroxypropyl, neopentyl, 1,1-dimethyl-2-hydroxyethyl, 1-(hydroxymethyl)propyl, 2-methylpropyl, cyclopropylmethyl, cyclobutyl, 1,2-dimethyl-2-hydroxypropyl, or 1-(hydroxymethyl)-2-hydroxyethyl and $R^2$ is 2-hydroxyethyl, 3-hydroxypropyl, 2-hydroxypropyl, 1-(2-hydroxyethyl)-3-hydroxypropyl, or 2-oxopropyl.

In one embodiment the present invention provides a compound of formula I wherein $Ar^1$ is aryl, $X^1$ is O, $R^1$ is (R)-2-hydroxy-1-methylethyl or (S)-2-hydroxy-1-methylethyl and $R^2$ is 2-oxopropyl, (R)-2-hydroxypropyl or (S)-2-hydroxypropyl.

In one embodiment the present invention provides a compound of formula I wherein $Ar^1$ is aryl, $X^1$ is O and $R^1$ is hydroxyalkyl. In another embodiment the present invention provides a compound of formula I wherein $Ar^1$ is aryl, $X^1$ is O, $R^1$ is hydroxyalkyl and $R^2$ is hydroxyalkyl.

In still another embodiment the present invention provides a compound of formula I wherein $Ar^1$ is aryl, $X^1$ is O, $R^1$ is hydroxyalkyl and $R^2$ is 2-hydroxyethyl, 3-hydroxypropyl, 2-hydroxypropyl, or 1-(2-hydroxyethyl)-3-hydroxypropyl.

In another embodiment the present invention provides a compound of formula I wherein $Ar^1$ is aryl, $X^1$ is O;

$R^1$ is (R)-2-hydroxy-1-methylethyl and $R^2$ is (R)-2-hydroxypropyl;

$R^1$ is (R)-2-hydroxy-1-methylethyl and $R^2$ is (S)-2-hydroxypropyl;

$R^1$ is (S)-2-hydroxy-1-methylethyl and $R^2$ is (R)-2-hydroxypropyl; or $R^1$ is (S)-2-hydroxy-1-methylethyl and $R^2$ is (S)-2-hydroxypropyl.

In one embodiment the present invention provides a compound of formula I wherein $R^1$ is hydroxyalkyl. In another embodiment the present invention provides a compound of formula I wherein $R^1$ is hydroxyalkyl and $R^2$ is hydroxyalkyl. In still another embodiment the present invention provides a compound of formula I wherein $R^1$ is hydroxyalkyl, $R^2$ is hydroxyalkyl and $Ar^1$ is aryl.

In one embodiment the present invention provides a compound of formula I wherein $R^2$ is hydroxyalkyl.

In certain embodiments, the compounds of the invention may be of the formula:

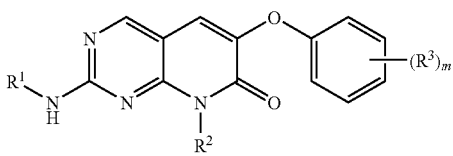

wherein:
m is from 0 to 4;
each $R^3$ is alkyl, halo, alkoxy or haloalkyl; and
$R^1$ and $R^2$ are as described herein.

In specific embodiments, m is 1 and $R^3$ is halo.

In still other embodiments, m is 2 and $R^3$ is halo.

In one embodiment the present invention provides a compound of formula II wherein $R^1$ is alkoxyalkyl, alkyl, cycloalkyl, cycloalkylalkyl, hydroxyalkyl, or heterocyclyl.

In one embodiment the present invention provides a compound of formula II wherein $R^1$ is tetrahydropyranyl, 1-methyl-2-methoxyethyl, cyclopentyl, cyclopropyl, iso-propyl, cyclohexyl, 1-(2-hydroxyethyl)-3-hydroxypropyl, 1-hydroxymethyl-2-hydroxypropyl, 1-hydroxymethyl-3-hydroxypropyl, 1-methylpropyl, 2-hydroxy-1-methylethyl, 1-(2-methoxyethyl)-3-methoxypropyl, N-methanesulfonyl piperidinyl, ethyl, methyl, 2-hydroxypropyl, neopentyl, 1,1-dimethyl-2-hydroxyethyl, 1-(hydroxymethyl)propyl, 2-methylpropyl, cyclopropylmethyl, cyclobutyl, 1,2-dimethyl-2-hydroxypropyl, or 1-(hydroxymethyl)-2-hydroxyethyl. In another embodiment the present invention provides a compound of formula II wherein $R^1$ is tetrahydropyranyl, 1-methyl-2-methoxyethyl, cyclopentyl, cyclopropyl, iso-propyl, cyclohexyl, 1-(2-hydroxyethyl)-3-hydroxypropyl, 1-hydroxymethyl-2-hydroxypropyl, 1-hydroxymethyl-3-hydroxypropyl, 1-methylpropyl, 2-hydroxy-1-methylethyl, 1-(2-methoxyethyl)-3-methoxypropyl, N-methanesulfonyl piperidinyl, ethyl, methyl, 2-hydroxypropyl, neopentyl, 1,1-dimethyl-2-hydroxyethyl, 1-(hydroxymethyl)propyl, 2-methylpropyl, cyclopropylmethyl, cyclobutyl, 1,2-dimethyl-2-hydroxypropyl, or 1-(hydroxymethyl)-2-hydroxyethyl and $R^2$ is 2-hydroxyethyl, 3-hydroxypropyl, 2-hydroxypropyl, 1-(2-hydroxyethyl)-3-hydroxypropyl, or 2-oxopropyl.

In one embodiment the present invention provides a compound of formula II wherein $R^1$ is (R)-2-hydroxy-1-methylethyl or (S)-2-hydroxy-1-methylethyl and $R^2$ is 2-oxopropyl, (R)-2-hydroxypropyl or (S)-2-hydroxypropyl.

In one embodiment the present invention provides a compound of formula II wherein $R^1$ and $R^2$ are hydroxyalkyl.

In one embodiment the present invention provides a compound of formula II wherein:

$R^1$ is (R)-2-hydroxy-1-methylethyl and $R^2$ is (R)-2-hydroxypropyl;

$R^1$ is (R)-2-hydroxy-1-methylethyl and $R^2$ is (S)-2-hydroxypropyl;

$R^1$ is (S)-2-hydroxy-1-methylethyl and $R^2$ is (R)-2-hydroxypropyl; or $R^1$ is (S)-2-hydroxy-1-methylethyl and $R^2$ is (S)-2-hydroxypropyl.

In another embodiment the present invention provides a compound of formula II wherein $R^1$ and $R^2$ are hydroxyalkyl, n is 1 and $R^3$ is halo.

In another embodiment the present invention provides a compound of formula II wherein $R^1$ and $R^2$ are hydroxyalkyl, n is 2 and $R^3$ is halo.

Representative compounds in accordance with the invention are shown in Table I.

TABLE 1

| # | Structure | Name |
|---|-----------|------|
| 1 | 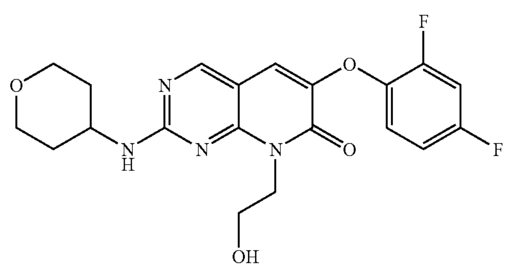 | 6-(2,4-Difluoro-phenoxy)-8-(2-hydxoxy-ethyl)-2-(tetrahydro-pyran-4-ylamino)-8H-pyrido[2,3-d]pyrimidin-7-one |
| 2 | 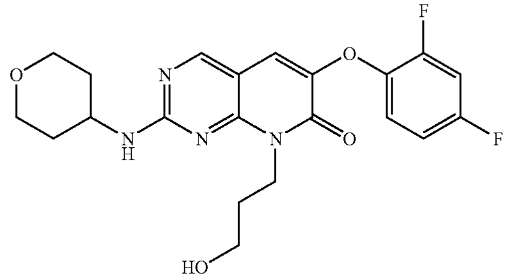 | 6-(2,4-Difluoro-phenoxy)-8-(3-hydroxy-propyl)-2-(tetrahydro-pyran-4-ylamino)-8H-pyrido[2,3-d]pyrimidin-7-one |

TABLE 1-continued

| # | Structure | Name |
|---|---|---|
| 3 | 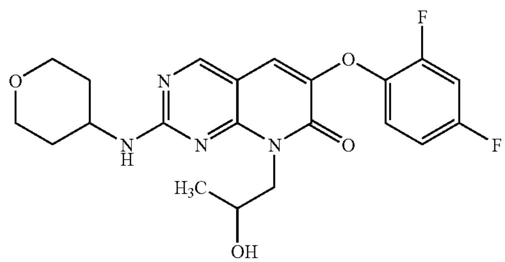 | 6-(2,4-Difluoro-phenoxy)-8-(2-hydroxy-propyl)-2-(tetrahydro-pyran-4-ylamino)-8H-pyrido[2,3-d]pyrimidin-7-one |
| 4 | 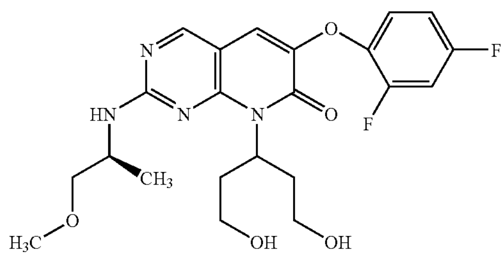 | 6-(2,4-Difluoro-phenoxy)-8-[3-hydroxy-1-(2-hydroxy-ethyl)-propyl]-2-((S)-2-methoxy-1-methyl-ethylamino)-8H-pyrido[2,3-d]pyrimidin-7-one |
| 5 | 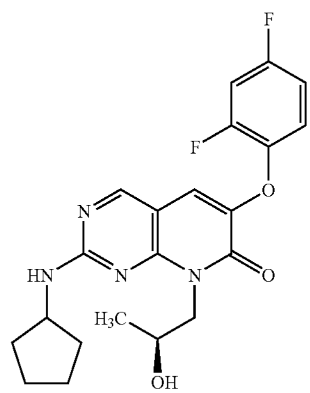 | 2-Cyclopentylamino-6-(2,4-difluoro-phenoxy)-8-((S)-2-hydroxy-propyl)-8H-pyrido[2,3-d]pyrimidin-7-one |
| 6 | 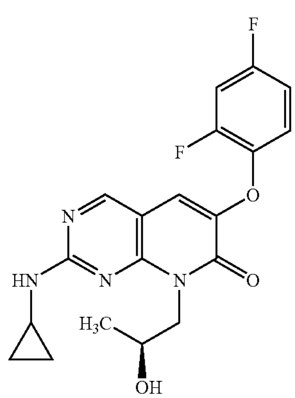 | 2-Cyclopropylamino-6-(2,4-difluoro-phenoxy)-8-((S)-2-hydroxy-propyl)-8H-pyrido[2,3-d]pyrimidin-7-one |

TABLE 1-continued

| # | Structure | Name |
|---|---|---|
| 7 | 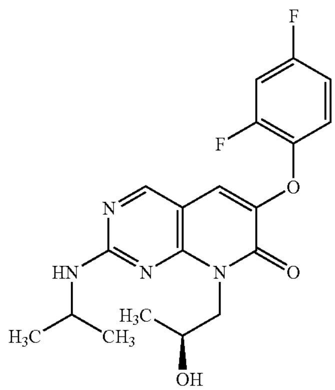 | 6-(2,4-Difluoro-phenoxy)-8-((S)-2-hydroxy-propyl)-2-isopropylamino-8H-pyrido[2,3-d]pyrimidin-7-one |
| 8 | 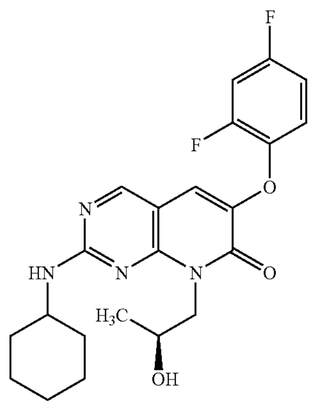 | 2-Cyclohexylamino-6-(2,4-difluoro-phenoxy)-8-((S)-2-hydroxy-propyl)-8H-pyrido[2,3-d]pyrimidin-7-one |
| 9 | 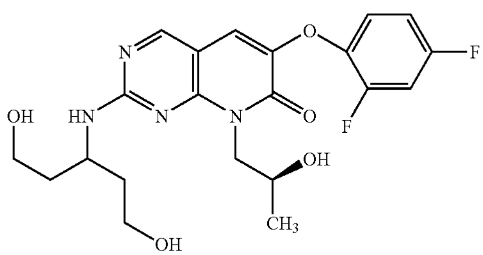 | 6-(2,4-Difluoro-phenoxy)-2-[3-hydroxy-1-(2-hydroxy-ethyl)-propylamino]-8-((S)-2-hydroxy-propyl)-8H-pyrido[2,3-d]pyrimidin-7-one |
| 10 | 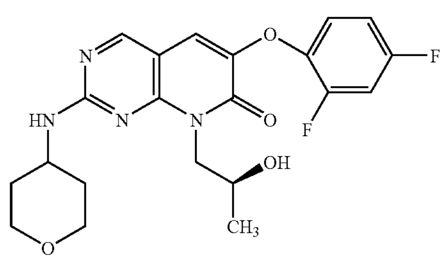 | 6-(2,4-Difluoro-phenoxy)-8-((S)-2-hydroxy-propyl)-2-(tetrahydro-pyran-4-ylamino)-8H-pyrido[2,3-d]pyrimidin-7-one |
| 11 | 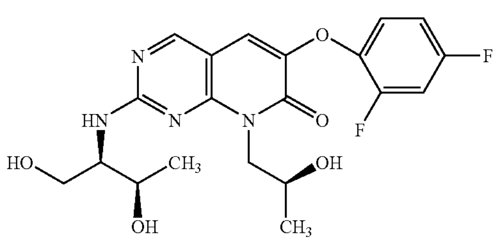 | 6-(2,4-Difluoro-phenoxy)-2-((1R,2R)-2-hydroxy-1-hydroxymethyl-propylamino)-8-((S)-2-hydroxy-propyl)-8H-pyrido[2,3-d]pyrimidin-7-one |

TABLE 1-continued

| # | Structure | Name |
|---|---|---|
| 12 | 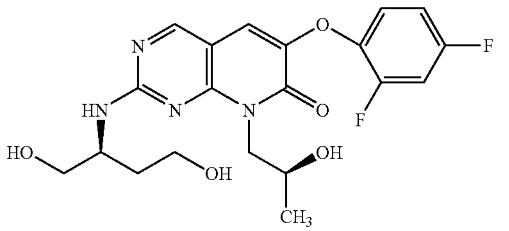 | 6-(2,4-Difluoro-phenoxy)-2-((S)-3-hydroxy-1-hydroxymethyl-propylamino)-8-((S)-2-hydroxy-propyl)-8H-pyrido[2,3-d]pyrimidin-7-one |
| 13 | 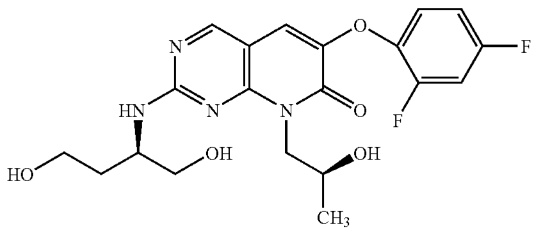 | 6-(2,4-Difluoro-phenoxy)-2-((R)-3-hydroxy-1-hydroxymethyl-propylamino)-8-((S)-2-hydroxy-propyl)-8H-pyrido[2,3-d]pyrimidin-7-one |
| 14 | 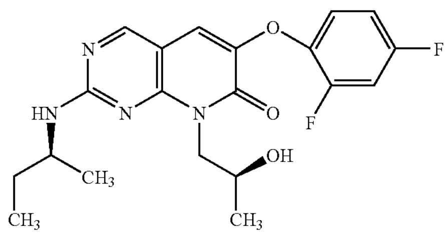 | 2-((S)-sec-Butylamino)-6-(2,4-difluoro-phenoxy)-8-((S)-2-hydroxy-propyl)-8H-pyrido[2,3-d]pyrimidin-7-one |
| 15 | 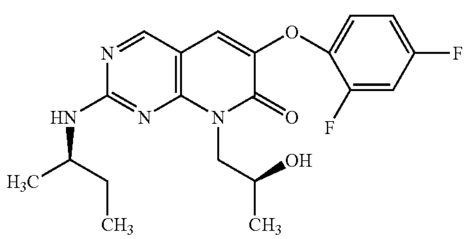 | 2-((R)-sec-Butylamino)-6-(2,4-difluoro-phenoxy)-8-((S)-2-hydroxy-propyl)-8H-pyrido[2,3-d]pyrinaidin-7-one |
| 16 | 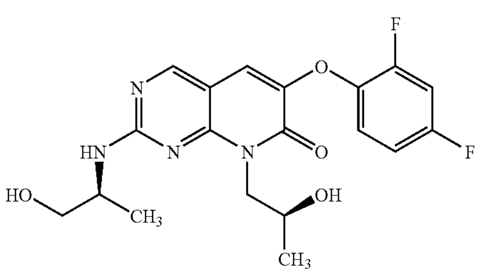 | 6-(2,4-Difluoro-phenoxy)-2-((S)-2-hydroxy-1-methyl-ethylamino)-8-((S)-2-hydroxy-propyl)-8H-pyrido[2,3-d]pyrimidin-7-one |
| 17 | 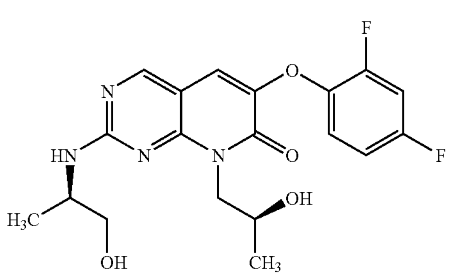 | 6-(2,4-Difluoro-phenoxy)-2-((R)-2-hydroxy-1-methyl-ethylamino)-8-((S)-2-hydroxy-propyl)-8H-pyrido[2,3-d]pyrimidin-7-one |

TABLE 1-continued

| # | Structure | Name |
|---|---|---|
| 18 | 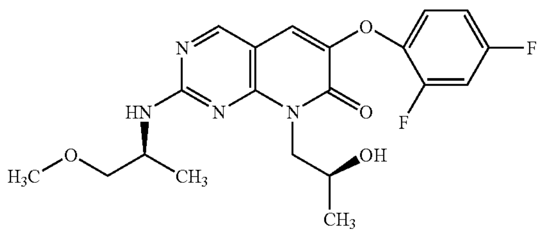 | 6-(2,4-Difluoro-phenoxy)-8-((S)-2-hydroxy-propyl)-2-((S)-2-methoxy-1-methyl-ethylamino)-8H-pyrido[2,3-d]pyrimidin-7-one |
| 19 | 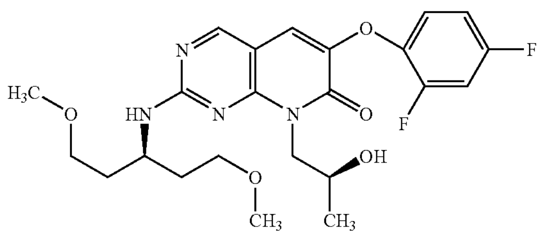 | 6-(2,4-Difluoro-phenoxy)-8-((S)-2-hydroxy-propyl)-2-[3-methoxy-1-(2-methoxy-ethyl)-propylamino]-8H-pyrido[2,3-d]pyrimidin-7-one |
| 20 | 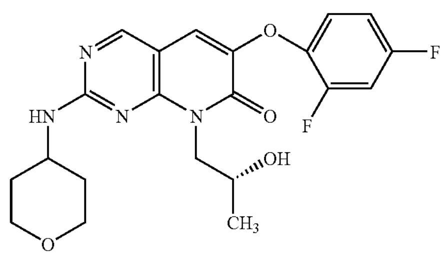 | 6-(2,4-Difluoro-phenoxy)-8-((R)-2-hydroxy-propyl)-2-(tetrahydro-pyran-4-ylamino)-8H-pyrido[2,3-d]pyrimidin-7-one |
| 21 | 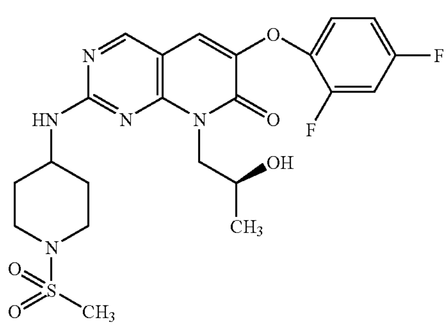 | 6-(2,4-Difluoro-phenoxy)-8-((S)-2-hydroxy-propyl)-2-(1-methanesulfonyl-piperidin-4-ylamino)-8H-pyrido[2,3-d]pyrimidin-7-one |
| 22 | 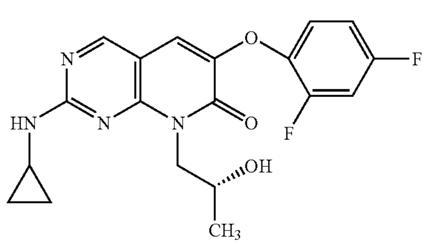 | 2-Cyclopropylamino-6-(2,4-difluoro-phenoxy)-8-((R)-2-hydroxy-propyl)-8H-pyrido[2,3-d]pyrimidin-7-one |
| 23 | 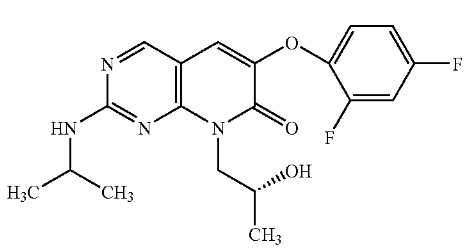 | 6-(2,4-Difluoro-phenoxy)-8-((R)-2-hydroxy-propyl)-2-isopropylamino-8H-pyrido[2,3-d]pyrimidin-7-one |

TABLE 1-continued

| # | Structure | Name |
|---|-----------|------|
| 24 | 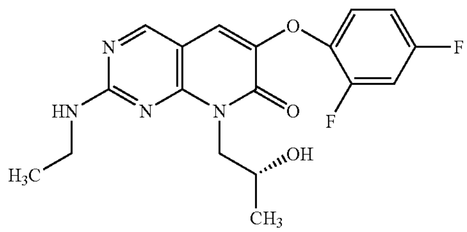 | 6-(2,4-Difluoro-phenoxy)-2-ethylamino-8-((R)-2-hydroxy-propyl)-8H-pyrido[2,3-d]pyrimidin-7-one |
| 25 | 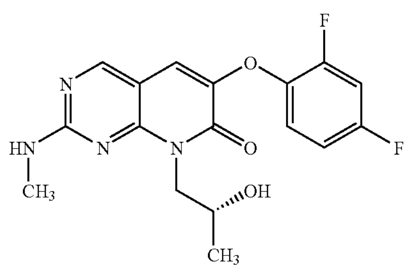 | 6-(2,4-Difluoro-phenoxy)-8-((R)-2-hydroxy-propyl)-2-methylamino-8H-pyrido[2,3-d]pyrimidin-7-one |
| 26 | 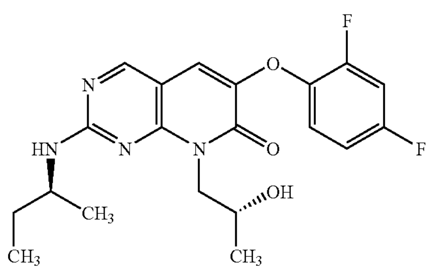 | 2-((S)-sec-Butylamino)-6-(2,4-difluoro-phenoxy)-8-((R)-2-hydroxy-propyl)-8H-pyrido[2,3-d]pyrimidin-7-one |
| 27 | 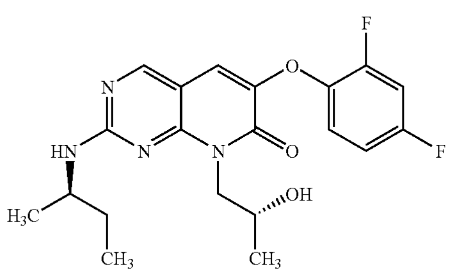 | 2-((R)-sec-Butylamino)-6-(2,4-difluoro-phenoxy)-8-((R)-2-hydroxy-propyl)-8H-pyrido[2,3-d]pyrimidin-7-one |
| 28 | 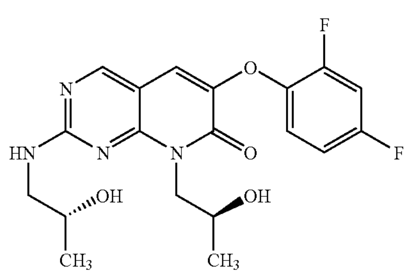 | 6-(2,4-Difluoro-phenoxy)-8-((S)-2-hydroxy-propyl)-2-((R)-2-hydroxy-propylamino)-8H-pyrido[2,3-d]pyrimidin-7-one |
| 29 | 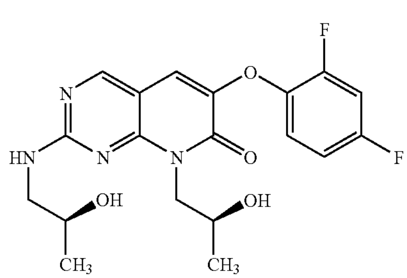 | 6-(2,4-Difluoro-phenoxy)-8-((S)-2-hydroxy-propyl)-2-((S)-2-hydroxy-propylamino)-8H-pyrido[2,3-d]pyrimidin-7-one |

TABLE 1-continued

| # | Structure | Name |
|---|---|---|
| 30 | 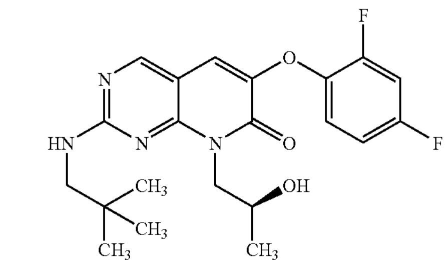 | 6-(2,4-Difluoro-phenoxy)-2-(2,2-dimethyl-propylamino)-8-((S)-2-hydroxy-propyl)-8H-pyrido[2,3-d]pyrimidin-7-one |
| 31 | 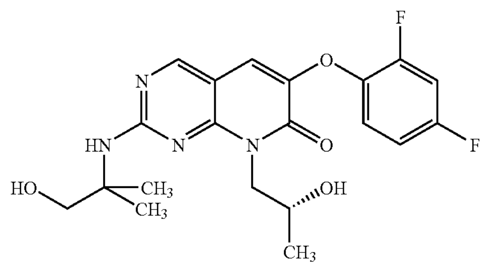 | 6-(2,4-Difluoro-phenoxy)-2-(2-hydroxy-1,1-dimethyl-ethylamino)-8-((R)-2-hydroxy-propyl)-8H-pyrido[2,3-d]pyrimidin-7-one |
| 32 | 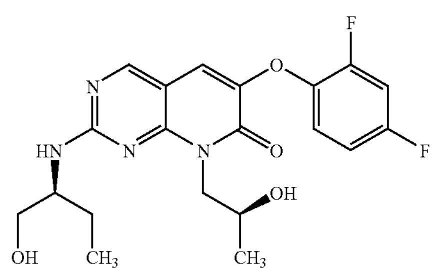 | 6-(2,4-Difluoro-phenoxy)-2-((S)-1-hydroxymethyl-propylamino)-8-((S)-2-hydroxy-propyl)-8H-pyrido[2,3-d]pyrimidin-7-one |
| 33 | 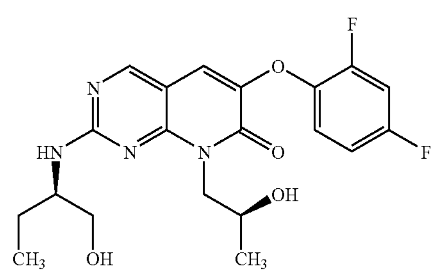 | 6-(2,4-Difluoro-phenoxy)-2-((R)-1-hydroxymethyl-propylamino)-8-((S)-2-hydroxy-propyl)-8H-pyrido[2,3-d]pyrimidin-7-one |
| 34 | 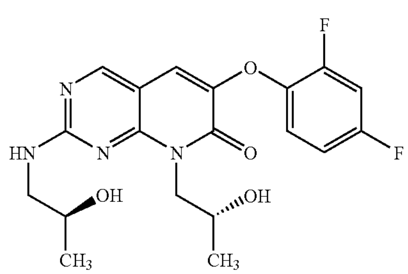 | 6-(2,4-Difluoro-phenoxy)-8-((R)-2-hydroxy-propyl)-2-((S)-2-hydroxy-propylamino)-8H-pyrido[2,3-d]pyrimidin-7-one |

TABLE 1-continued

| # | Structure | Name |
|---|---|---|
| 35 | 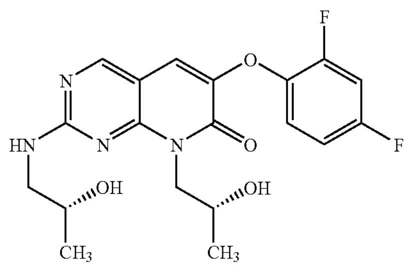 | 6-(2,4-Difluoro-phenoxy)-8-((R)-2-hydroxy-propyl)-2-((R)-2-hydroxy-propylamino)-8H-pyrido[2,3-d]pyrimidin-7-one |
| 36 | 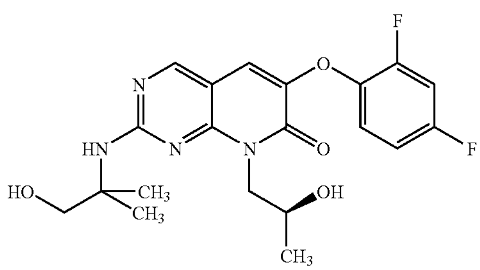 | 6-(2,4-Difluoro-phenoxy)-2-(2-hydroxy-1,1-dimethyl-ethylamino)-8-((S)-2-hydroxy-propyl)-8H-pyrido[2,3-d]pyrimidin-7-one |
| 37 | 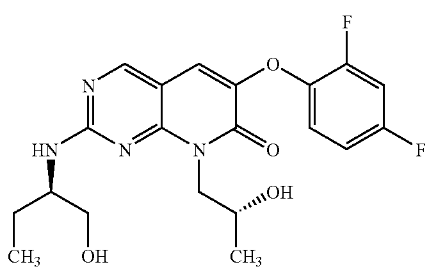 | 6-(2,4-Difluoro-phenoxy)-2-((R)-1-hydroxymethyl-propylamino)-8-((R)-2-hydroxy-propyl)-8H-pyrido[2,3-d]pyrimidin-7-one |
| 38 | 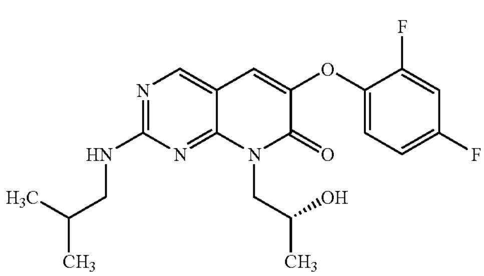 | 6-(2,4-Difluoro-phenoxy)-8-((R)-2-hydroxy-propyl)-2-isobutylamino-8H-pyrido[2,3-d]pyrimidin-7-one |
| 39 | 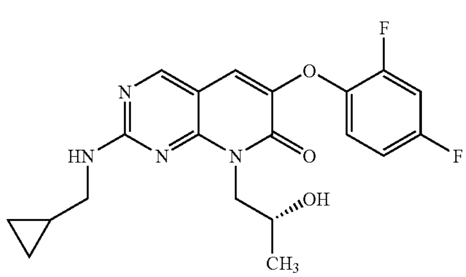 | 2-(Cyclopropylmethyl-amino)-6-(2,4-difluoro-phenoxy)-8-((R)-2-hydroxy-propyl)-8H-pyrido[2,3-d]pyrimidin-7-one |

TABLE 1-continued

| # | Structure | Name |
|---|---|---|
| 40 | 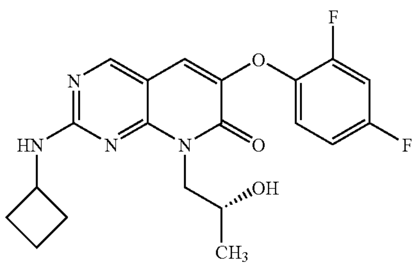 | 2-Cyclobutylamino-6-(2,4-difluoro-phenoxy)-8-((R)-2-hydroxy-propyl)-8H-pyrido[2,3-d]pyrimidin-7-one |
| 41 | 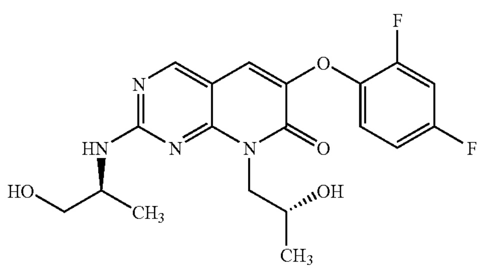 | 6-(2,4-Difluoro-phenoxy)-2-((S)-2-hydroxy-1-methyl-ethylamino)-8-((R)-2-hydroxy-propyl)-8H-pyrido[2,3-d]pyrimidin-7-one |
| 42 | 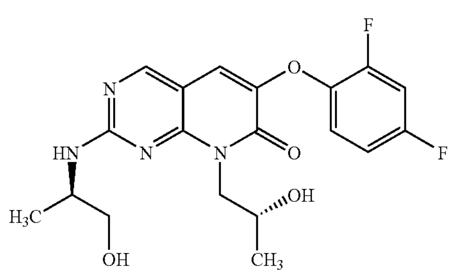 | 6-(2,4-Difluoro-phenoxy)-2-((R)-2-hydroxy-1-methyl-ethylamino)-8-((R)-2-hydroxy-propyl)-8H-pyrido[2,3-d]pyrimidin-7-one |
| 43 | 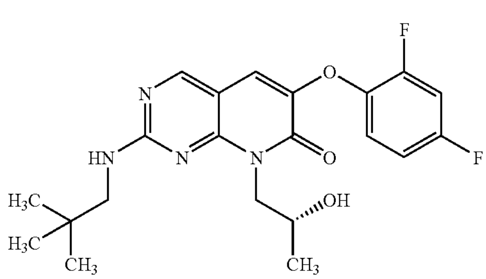 | 6-(2,4-Difluoro-phenoxy)-2-(2,2-dimethyl-propylamino)-8-((R)-2-hydroxy-propyl)-8H-pyrido[2,3-d]pyrimidin-7-one |

TABLE 1-continued

| # | Structure | Name |
|---|---|---|
| 44 | 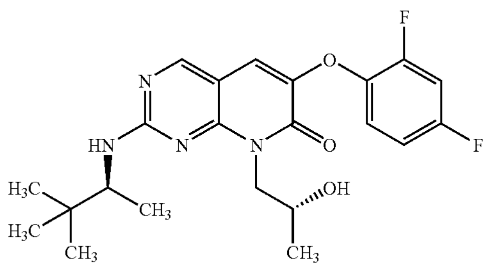 | 6-(2,4-Difluoro-phenoxy)-2-((S)-2-hydroxy-1,2-dimethyl-propylamino)-8-((R)-2-hydroxy-propyl)-8H-pyrido[2,3-d]pyrimidin-7-one |
| 45 | 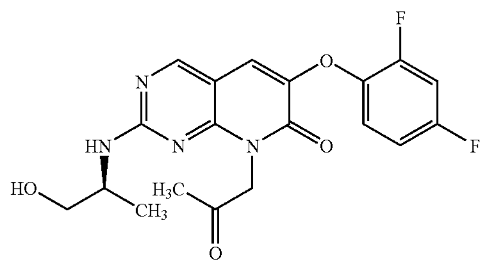 | 6-(2,4-Difluoro-phenoxy)-2-((S)-2-hydroxy-1-methyl-ethylamino)-8-(2-oxo-propyl)-8H-pyrido[2,3-d]pyrimidin-7-one |
| 46 | 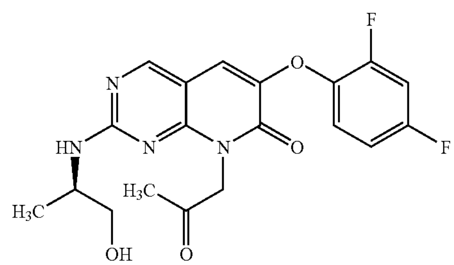 | 6-(2,4-Difluoro-phenoxy)-2-((R)-2-hydroxy-1-methyl-ethylamino)-8-(2-oxo-propyl)-8H-pyrido[2,3-d]pyrimidin-7-one |
| 47 | 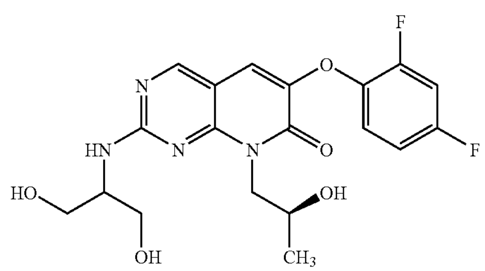 | 6-(2,4-Difluoro-phenoxy)-2-(2-hydroxy-1-hydroxymethyl-ethylamino)-8-((S)-2-bydroxy-propyl)-8H-pyrido[2,3-d]pyrimidin-7-one |

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes can be made without departing from the spirit or scope of the invention.

Processes for Preparing the Compounds

The compounds of the present invention can be prepared by a variety of methods including by methods disclosed in commonly assigned U.S. patent application Ser. No. 10/073,845, which was previously incorporated by reference. In one aspect of the present invention, a method for preparing compounds of Formula I is shown in Scheme 1 below. It should be appreciated that although the scheme often indicates exact structures, methods of the present invention apply widely to analogous compounds of Formula I, given appropriate consideration to protection and deprotection of reactive functional groups by methods standard to the art of organic chemistry. For example, hydroxy groups, in order to prevent unwanted side reactions, sometimes need to be protected (e.g., converted to ethers or esters) during chemical reactions at other sites in the molecule. The hydroxy protecting group is then removed to provide the free hydroxy group. Similarly, amino groups and carboxylic acid groups can be protected (e.g., by derivatization) to protect them against unwanted side reactions. Typical protecting groups, and methods for attaching and cleaving them, are described fully in the above incorporated references by T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996).

Scheme 1

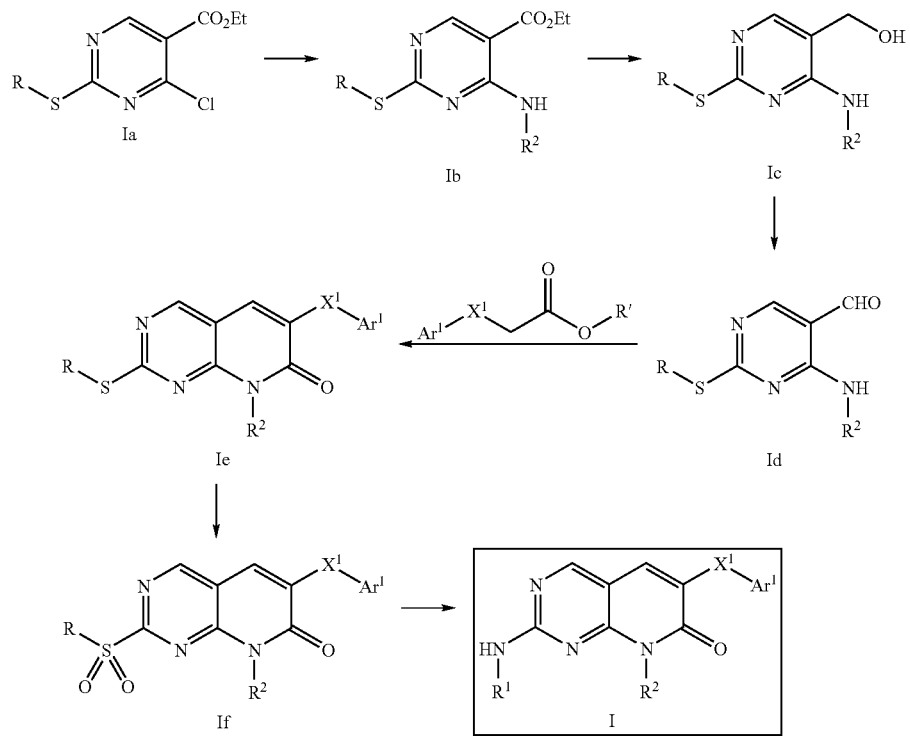

Treatment of a compound of Formula Ia with a hydroxyalkyl amine ($R^2$—$NH_2$) provides a compound of Formula Ib. This reaction is conveniently carried out in a solvent which is inert under the reaction conditions, preferably a halogenated aliphatic hydrocarbon, especially dichloromethane, an optionally halogenated aromatic hydrocarbon, or an open-chain or cyclic ether such as tetrahydrofuran (THF), a formamide or a lower alkanol. Suitably, the reaction is carried out at about −20° C. to about 120° C., typically at about 0° C. Often a base, such as trialkyl amine, preferably triethylamine, is added to the reaction mixture.

Reduction of a compound of Formula Ib provides an alcohol of Formula Ic. This reduction is typically carried out using lithium aluminum hydride in a manner well known to those of skill in the art (e.g., in a solvent that is inert under the conditions of the reduction, preferably an open-chain or cyclic ether, especially tetrahydrofuran, at about −20° C. to about 70° C., preferably at about 0° C. to about room temperature).

Oxidation of an alcohol of Formula Ic provides a carboxaldehyde of Formula Id. The oxidation is typically carried out with manganese dioxide, although numerous other methods can also be employed (see, for example, ADVANCED ORGANIC CHEMISTRY, 4$^{TH}$ ED., March, John Wiley & Sons, New York (1992)). Depending on the oxidizing agent employed, the reaction is carried out conveniently in a solvent which is inert under the specific oxidation conditions, preferably a halogenated aliphatic hydrocarbon, especially dichloromethane, or an optionally halogenated aromatic hydrocarbon. Suitably, the oxidation is carried out at about 0° C. to about 60° C.

Reaction of a carboxaldehyde of Formula Id with an ester, $Ar^1$—$X^1CH_2$—$CO_2R'$ (where R' is an alkyl group, and $Ar^1$ and $X^1$ are those defined herein) in the presence of a base provides a compound of Formula Ie. Any relatively non-nucleophilic base can be used including carbonates, such as potassium carbonate, lithium carbonate, and sodium carbonate; bicarbonates, such as potassium bicarbonate, lithium bicarbonate, and sodium bicarbonate; amines, such as secondary and tertiary amines; and resin bound amines such as 1,3,4,6,7,8-hexahydro-2H pyrimido[1,2-a]pyrimidine. Conveniently, the reaction is carried out in a solvent which is relatively polar but inert under the reaction conditions, preferably an amide such as dimethyl formamide, N-substituted pyrrolidinone, especially 1-methyl-2-pyrrolidinone, and at a temperature of about 25° C. to about 150° C.

Oxidation of Ie with an oxidizing agent, e.g., a peracid such as 3-chloroperbenzoic acid (i.e., MCPBA) or Oxone®, provides a sulfone (If) which can be converted to a variety of target compounds. Typically the oxidation of Ie is carried out in a solvent which is inert under the conditions of the oxidation. For example, when MCPBA is used as the oxidizing agent, the solvent is preferably a halogenated aliphatic hydrocarbon, especially chloroform. When Oxone® is used as the oxidizing agent, the solvent is preferably methanol, aqueous ethanol or aqueous tetrahydrofuran. The reaction temperature depends on the solvent used. For an organic solvent, the reaction temperature is generally at about −20° C. to about 50° C., preferably about 0° C. to about room temperature. When water is used as the solvent, the reaction temperature is generally from about 0° C. to about 50° C., preferably about 0° C. to about room temperature. Alternatively, the oxidation may be carried under catalytic conditions with rhenium/peroxide based reagents, see ("Oxidation of Sulfoxides by Hydrogen Peroxide, Catalyzed by Methyltrioxorhenium (VII)", Lahti et al., Inorg. Chem., 2000, 39, 2164-2167; "Rhenium oxo complexes in catalytic oxidations, Catal. Today, 2000, 55, 317-363, and "A Simple and Efficient Method for the Preparation of Pyridine N-Oxides", Coperet et al., *J. Org. Chem.,* 1998, 63, 1740-1741.

Reacting the compound If with an amine ($R^1$—$NH_2$) provides the compounds of Formula I. The reaction can be carried out in the presence or absence of solvent. Conveniently, the reaction is carried out at temperatures of from about 0° C. to about 200° C., more preferably about room temperature to about 150° C. Alternatively, in some cases rather than using the sulfone If, the sulfide Ie or the corresponding sulfoxide can be reacted directly with an amine ($R^1$—$NH_2$) to provide the compounds of Formula I.

One of skill in the art will understand that certain modifications to the above schemes are contemplated and within the scope of the present invention. For example, certain steps will involve the use of protecting groups for functional groups that are not compatible with particular reaction conditions.

Alternatively, compounds of Formula I can also be prepared by the method shown in Scheme 2 below. While the reactions of Scheme 2 are shown in terms of specific compounds, it will be readily apparent to those skilled in the art that the method of Scheme 2 may be used with all of the compounds of the invention.

As shown in Scheme 2, treatment of a diethyl acetal IIa with a thiourea provides a pyrimidine compound IIb. This reaction is conveniently carried out in an alcoholic solvent in the presence of a base, such as sodium methoxide. Methylation of the thiol group, e.g., with methyl iodide, then provides thioether IIc.

The thioether IIc may then be treated with an α-aryloxyester IId such as ethyl (2,4-difluorophenoxy)acetate to afford a pyrido-pyrimidone thioether IIe. This reaction may be carried out, for example, by heating in the presence sodium carbonate or other mild base in n-methylpyrrolidinone or other polar aprotic solvent.

Reaction of thioether IIe with propylene carbonate or like carbonate, under polar aprotic solvent conditions, to yield an N-hyrdoxyalkyl pyrido-pyrimidone thioether IIf. This reaction may be facilitated by heating in the presence of potassium carbonate.

The thioether IIf is then oxidized to provide the corresponding pyrido-pyrimidone sulfone IIg. This oxidation may be carried out using hydrogen peroxide in the presence of acetic acid in polar solvent such as methylene dichloride. The oxidation may alternatively be carried out using Oxone® or MCPBA in the manner described above for Scheme 1.

Treatment of sulfone IIg with a hydroxyamine, wherein the hydroxyl group is suitably protected, affords a pyrido-pyrimidone compound IIh in accordance with the invention. This reaction may be carried out with heating as described above with reference to Scheme 1.

Scheme 2

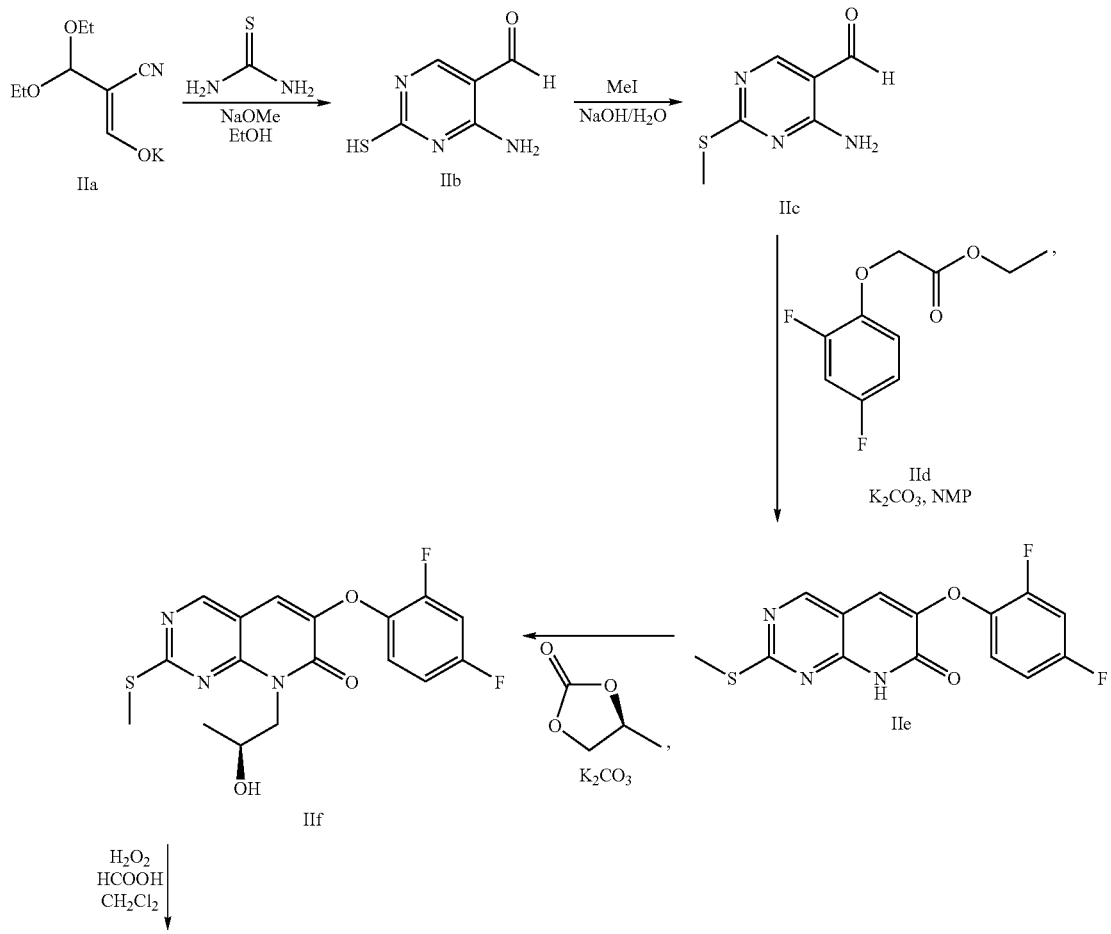

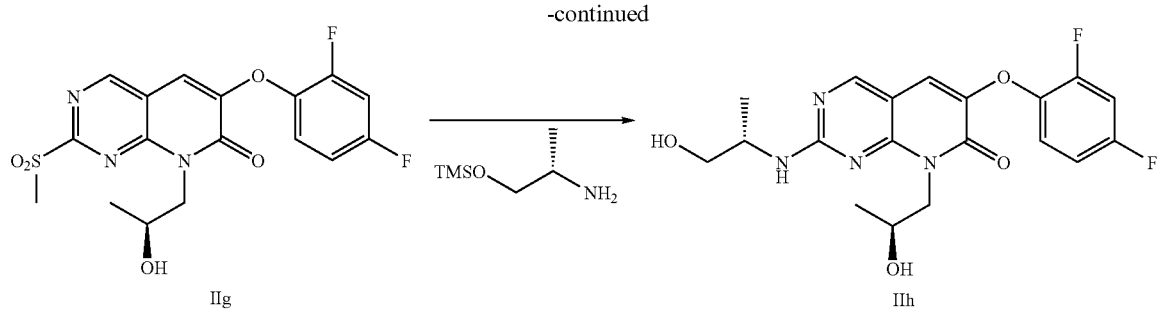

Pyridopyrimidinone IIf can also be prepared by alkylating pyridopyrimidinone IIe with an epoxide instead of a carbonate as shown in Scheme 3 below. The reaction of Scheme 3 may be carried out by heating compound IIe under pressure in the presence of excess propylene oxide in N-methylpyrrolidinone or under other polar aprotic solvent conditions.

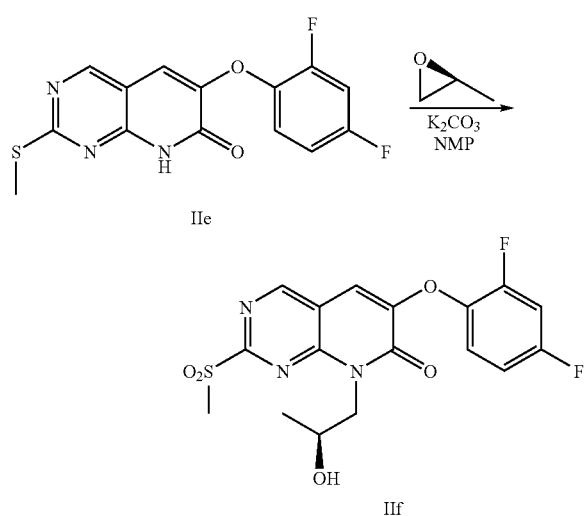

Pharmaceutical Compositions Containing the Compounds

The compounds of Formula I can be used as medicaments, e.g., in the form of pharmaceutical preparations. The pharmaceutical preparations can be administered enterally, e.g., orally in the form of tablets, coated tablets, dragées, hard and soft gelatine capsules, solutions, emulsions or suspensions, nasally, e.g., in the form of nasal sprays, or rectally, e.g., in the form of suppositories. However, they may also be administered parenterally, e.g., in the form of injection solutions.

The compounds of Formula I can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of Formula I.

Medicaments which contain a compound of Formula I with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of Formula I can be used in accordance with the invention as therapeutically active substances, especially as anti-inflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of Formula I for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I are useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarhritis, psoriatic arthritis, ankylosing spondylitis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion-injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; opthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

Additional objects, advantages, and novel features of this invention will become apparent to those skilled in the art upon examination of the following illustrative examples thereof, which are not intended to be limiting.

Unless otherwise stated, all temperatures including melting points (i.e., MP) are in degrees celsius (° C.).

Example 1

Preparation of 6-(2,4-difluoro-phenoxy)-2-((S)-(+)-2-hydroxy-1-methyl-ethylamino)-8-((S)-2-hydroxy-propyl)-8H-pyrido[2,3-d]pryimidin-7-one

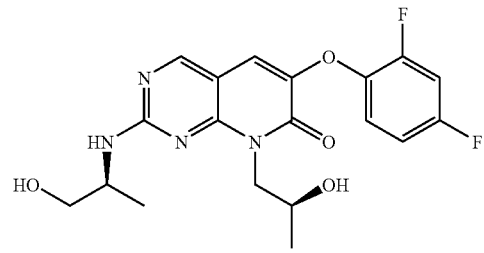

Step A: Preparation of ethyl-4-((S)-2-Hydroxy-propylamino)-2-methylsulfanyl-pyrimidine-5-carboxylate

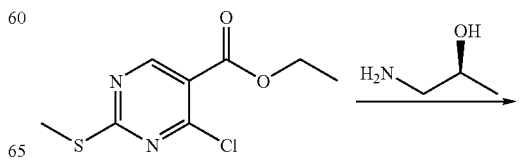

-continued

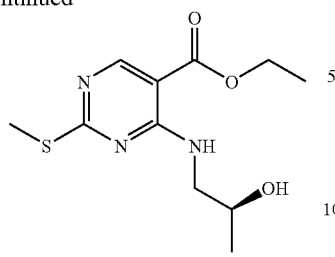

To a solution of ethyl 4-chloro-2-methylthiopyrimidine-5-carboxylate (Aldrich, 65 g, 280 mmol) in 500 mL of tetrahydrofuran at 0° C. was added triethylamine (140 mL 1000 mmol) and (S)-1-amino-2-propanol (21 g, 280 mmol). After stirring for 4 hours, water (200 mL) was added and the phases were separated. The aqueous layer was extracted with dichloromethane. The organic phase was concentrated and the residue was dissolved up with the dichloromethane and washed with brine and dried over magnesium sulfate. Filtered and the filtrate was evaporated under reduced pressure to give 77 g of the ethyl 4-(S)-2-hydroxy-propylamino)-2-methylsulfanyl pyrimidine-5-carboxylate as a white solid.

Step B: Preparation of 4-((S)-2-Hydroxy-propylamino)-2-methylsulfanyl pyrimidine-5-methanol

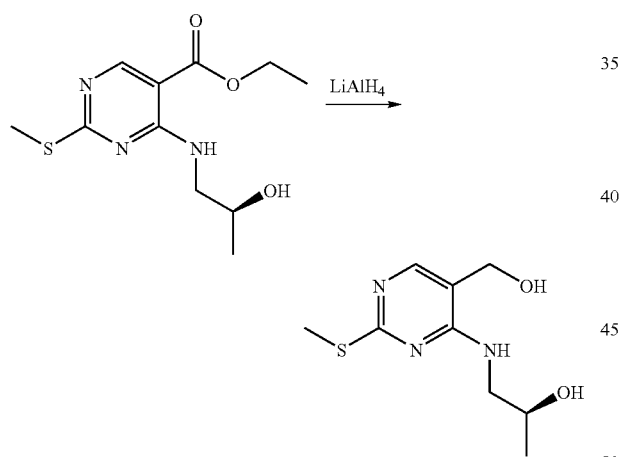

Lithium aluminum hydride (5.7 g, 150 mmol) was stirred in dry tetrahydrofuran (500 mL) at 5° C. and treated dropwise with a solution of ethyl 4-((S)-2-hydroxy-propylamino)-2-methylsulfanyl pyrimidine-5-carboxylate (27 g, 100 mmol) in dry tetrahydrofuran (450 mL). The reaction mixture was stirred for 15 minutes and then water (18 mL) was added dropwise with caution. The reaction was stirred for 30 minutes and then an aqueous solution of sodium hydroxide (15%, 8.5 mL) was added dropwise, followed by water (25.5 mL). The resulting suspension was stirred for 17 hours at room temperature and then filtered. The filter residue was washed with isopropanol (2×, 100 mL) and the combined filtrate and washings were evaporated under reduced pressure to give 25.8 g 4-((S)-2-hydroxy-propylamino)-2-methylsulfanyl pyrimidine-5-methanol.

Step C: Preparation of 4-((S)-2-Hydroxy-propylamino)-2-methylsulfanyl-pyrimidine-5-carbaldehyde

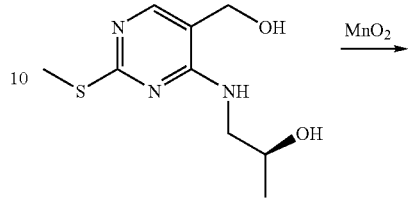

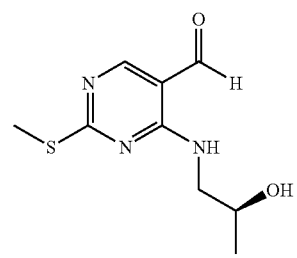

4-((S)-2-hydroxy-propylamino)-2-methylsulfanyl pyrimidine-5-methanol (26 g, 100 mmol) and 1 L of dichloromethane were combined with stirring and treated with manganese dioxide (102 g, 1 mol). The resulting suspension was stirred for 24 hours and then filtered through celite. The filter residue was washed with dichloromethane (100 mL) and the combined filtrate and washings were evaporated under reduced pressure to give 16.5 g of the 4-((S)-2-hydroxy-propylamino)-2-methylsulfanyl-pyrimidine-5-carbaldehyde as a white solid.

Sulfone

Step A: Preparation of 6-(2,4-Difluorophenoxy)-8-((S)-2-hydroxypropyl)-2-methylsulfanyl-8H-pyrido[2,3-d]pyrimidin-7-one

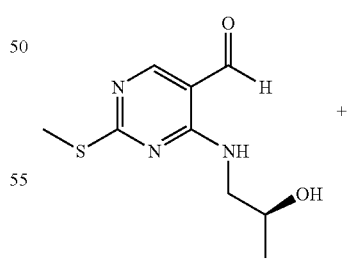

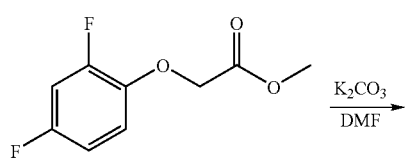

-continued

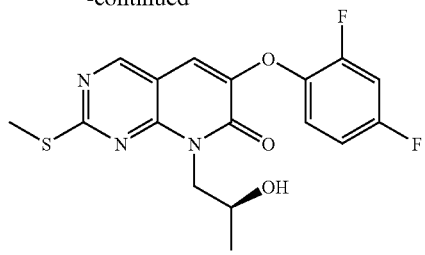

To a mixture of 4-((S)-2-hydroxy-propylamino)-2-methylsulfanyl-pyrimidine-5-carbaldehyde (16.5 g, 73 mmol) and (2,4-difluorophenoxy)acetic acid methyl ester (29.4 g, 145 mmol) in anhydrous dimethyl formamide (300 mL) was added potassium carbonate (30 g, 218 mmol). The reaction mixture was heated to 60° C. and after 18 hours, the reaction mixture was cooled and the dimethylformamide was distilled off under vacuum. Crude residue suspended in water (300 mL) and extracted with dichloromethane, washed with brine and dried over magnesium sulfate. Filtered and concentrated under vacuum to give 41 g crude material which was chromatographed on silica gel column eluding with 1% methanol in dichloromethane to give 30 g 6-(2,4-difluorophenoxy)-8-((S)-2-hydroxypropyl)-2-methylsulfanyl-8H-pyrido[2,3-d]pyrimidin-7-one (mass spec M+1=274).

Step B: Preparation of 6-(2,4-Difluorophenoxy)-8-((S)-2-hydroxypropyl)-2-methanesulfonyl-8H-pyrido[2,3-d]pyrimidin-7-one

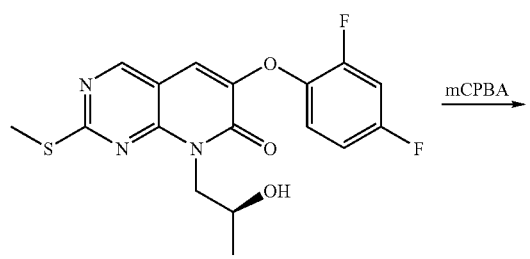

To a dichloromethane (500 mL) solution of 6-(2,4-difluorophenoxy)-8-((S)-2-hydroxypropyl)-2-methylsulfanyl-8H-pyrido[2,3-d]pyrimidin-7-one (29.7 g, 108 mmol) at 5° C. was added portionwise m-chloroperbenzoic acid (55 g, 240 mmol) and stirred for 24 hours. Reaction mixture washed with aqueous sodium sulfite, aqueous sodium bicarbonate and dried over magnesium sulfate. Filtered and evaporated to give 24 g 6-(2,4-difluorophenoxy)-8-((S)-2-hydroxypropyl)-2-methanesulfonyl-8H-pyrido[2,3-d]pyrimidin-7-one (mass spec M+1=412).

Step C: Preparation of 6-(2,4-Difluoro-phenoxy)-2-((S)-2-hydroxy-1-methyl-ethylamino)-8-((S)-2-hydroxy-propyl)-8H-pyrido[2,3-d]pyrimidin-7-one

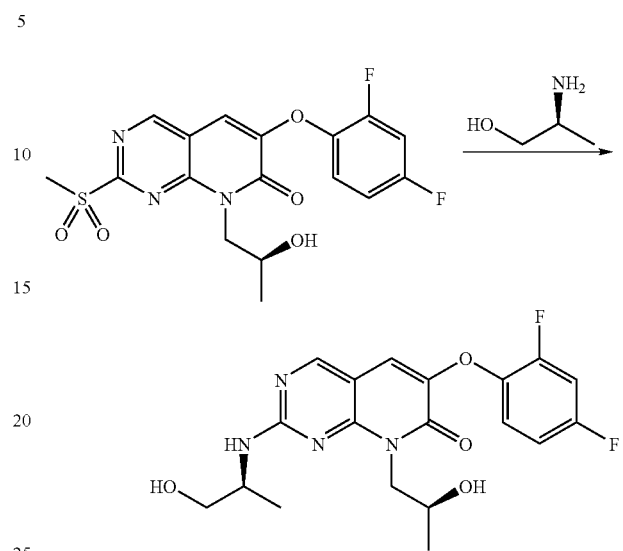

To a tetrahydrofuran (5 mL) solution of 6-(2,4-difluorophenoxy)-8-((S)-2-hydroxypropyl)-2-methanesulfonyl-8H-pyrido[2,3-d]pyrimidin-7-one (400 mg, 1 mmol) was added (S)-2-amino-1-propanol (0.38 mL, 5 mmol) and stirred overnight at room temperature. Concentrated under vacuum and chromatographed on silica gel eluding with 2% methanol in dichloromethane and converted to the hydrochloride salt to give 320 mg 6-(2,4-difluoro-phenoxy)-2-((S)-(+)-2-hydroxy-1-methyl-ethylamino)-8-((S)-2-hydroxy-propyl)-8H-pyrido[2,3-d]pyrimidin-7-one (mass spec. M+1=407, MP=175.1-179.1° C.).

Example 2

Preparation of 6-(2,4-Difluoro-phenoxy)-2-(R)-(−)-2-hydroxy-1-methyl-ethylamino)-8-((S)-2-hydroxy-propyl)-8H-pyrido[2,3-d]pyrimidin-7-one

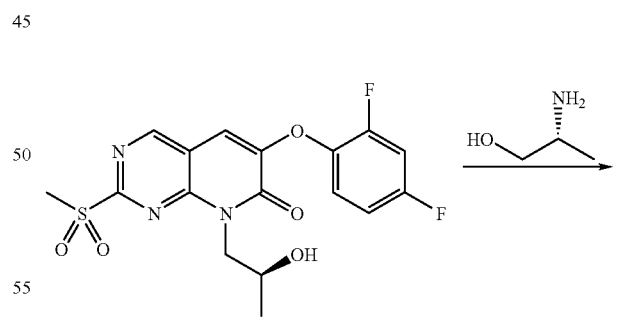

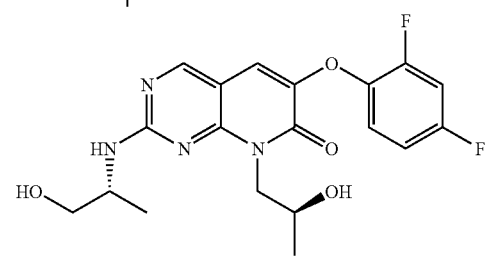

To a tetrahydrofuran (5 mL) solution of 6-(2,4-difluorophenoxy)-8-((S)-2-hydroxypropyl)-2-methanesulfonyl-8H-pyrido[2,3-d]pyrimidin-7-one (400 mg, 1 mmol) was added (R)-2-amino-1-propanol (0.38 mL, 5 mmol) and stirred overnight at room temperature. Concentrated under vacuum and chromatographed on silica gel eluding with 2% methanol in dichloromethane and converted to the hydrochloride salt to give 370 mg 6-(2,4-difluoro-phenoxy)-2-((R)-2-hydroxy-1-methyl-ethylamino)-8-((S)-2-hydroxy-propyl)-8H-pyrido[2,3-d]pyrimidin-7-one (mass spec. M+1=407, MP=174.9-178.1° C.).

Example 3

Preparation of 6-(2,4-Difluorophenoxy)-2-(2-hydroxy-1,1-dimethyl-ethylamino)-8-((S)-2-hydroxypropyl)-8H-pyrido[2,3-d]pyrimidin-7-one

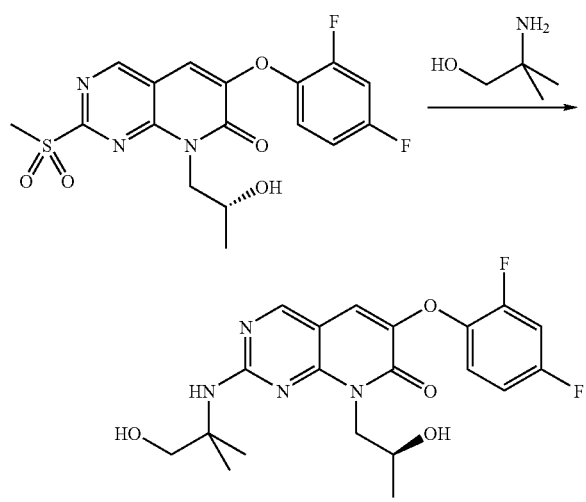

To a tetrahydrofuran (10 mL) solution of 6-(2,4-difluorophenoxy)-8-((S)-2-hydroxypropyl)-2-methanesulfonyl-8H-pyrido[2,3-d]pyrimidin-7-one (717 mg, 1.74 mmol) was added 2-amino-2-methyl-1-propanol (1.55 g, 17.43 mmol) and stirred at room temperature overnight, concentrated under vacuum and chromatographed on silica gel eluting with 4% methanol in dichloromethane to give, after converting to hydrochloride salt, 291 mg of 6-(2,4-difluorophenoxy)-2-(2-hydroxy-1,1-dimethyl-ethylamino)-8-((S)-2-hydroxy-propyl)-8H-pyrido[2,3-d]pyrimidin-7-one as a white solid (mass spec M+1=421, MP=187.4-189.9° C.).

Example 4

Preparation of 6-(2,4-difluoro-phenoxy)-2-((S)-2-hydroxy-1-methyl-ethylamino)-8-((R)-2-hydroxypropyl)-8H-pyrido[2,3-d]pyrimidin-7-one

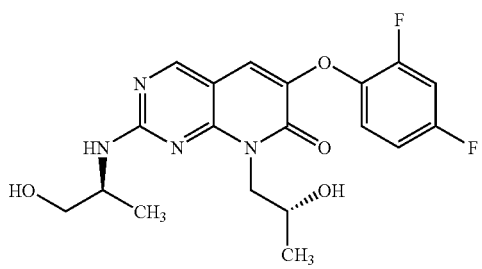

Step A: Preparation of ethyl-4-((R)-2-Hydroxy-propylamino)-2-methylsulfanyl-pyrimidine-5-carboxylate

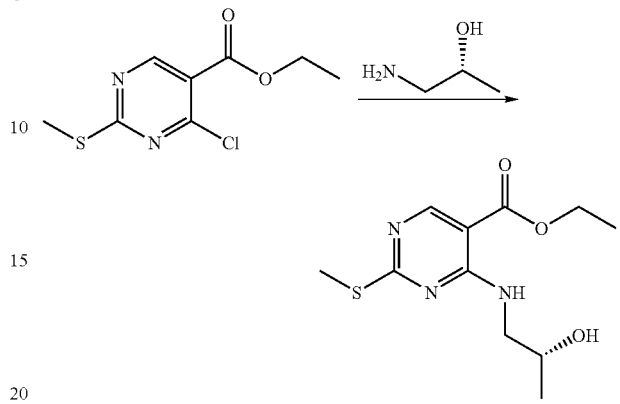

To a solution of ethyl 4-chloro-2-methylthiopyrimidine-5-carboxylate (Aldrich, 62.6 g, 269 mmol) in 1 L of THF at 0° C. was added triethylamine (135 mL 1000 mmol) and (R)-1-amino-2-propanol (30 g, 400 mmol). After stirring for 4 hours, evaporated under reduced pressure to give 66.6 g of the ethyl 4-(R)-2-hydroxy-propylamino)-2-methylsulfanyl pyrimidine-5-carboxylate as a white solid.

Step B: Preparation of 4-((R)-2-Hydroxy-propylamino)-2-methylsulfanyl pyrimidine-5-methanol

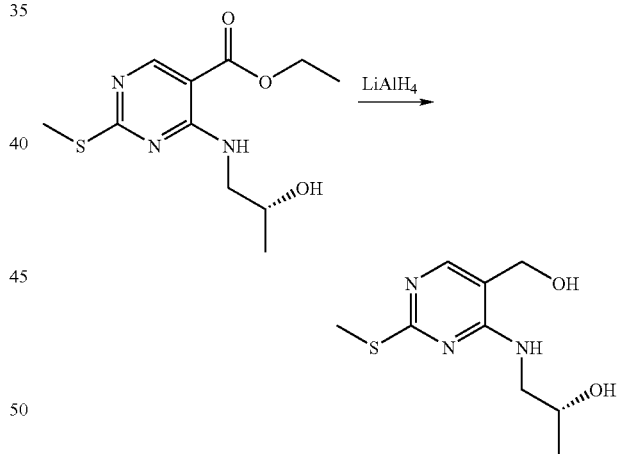

Lithium aluminum hydride (14 g, 368 mmol) was stirred in dry THF (500 mL) at 5° C. and treated dropwise with a solution of ethyl 4-(R)-2-hydroxy-propylamino)-2-methylsulfanyl pyrimidine-5-carboxylate (66.6 g, 246 mmol) in dry THF (150 mL). The reaction mixture was stirred for 15 min and then water (18 mL) was added dropwise with caution. The reaction was stirred for 30 min and then an aqueous solution of sodium hydroxide (15%, 8.5 mL) was added dropwise, followed by water (25.5 mL). The resulting suspension was stirred for 17 hours at RT and then filtered. The filter residue was washed with isopropanol (2×, 100 mL) and the combined filtrate and washings were evaporated under reduced pressure to give 58.6 g 4-(R)-2-hydroxy-propylamino)-2-methylsulfanyl pyrimidine-5-methanol.

Step C: Preparation of 4-((R)-2-Hydroxy-propylamino)-2-methylsulfanyl-pyrimidine-5-carbaldehyde

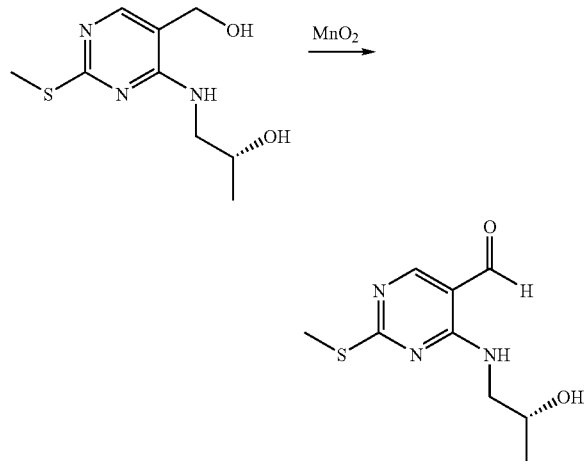

4-(R)-2-Hydroxy-propylamino)-2-methylsulfanyl pyrimidine-5-methanol (58.6 g, 256 mmol) and 1 L of dichloromethane were combined with stirring and treated with manganese dioxide (222 g, 2560 mol). The resulting suspension was stirred for 24 hours and then filtered through celite. The filter residue was washed with dichloromethane (100 mL) and the combined filtrate and washings were evaporated under reduced pressure to give 34 g of the 4-((R)-2-hydroxy-propylamino)-2-methylsulfanyl-pyrimidine-5-carbaldehyde as a white solid.

Sulfone

Step A: Preparation of 6-(2,4-Difluorophenoxy)-8-((R)-2-hydroxypropyl)-2-methylsulfanyl-8H-pyrido[2,3-d]pyrimidin-7-one

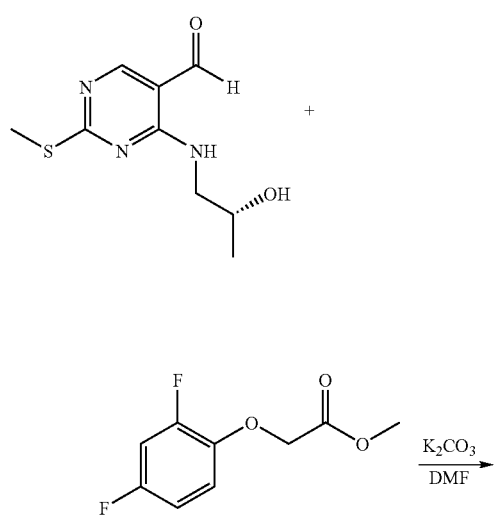

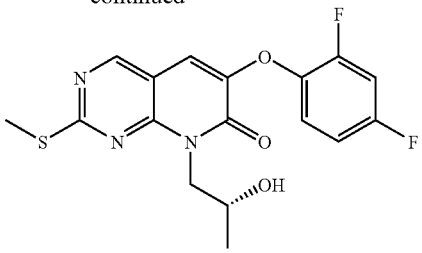

To a mixture of 4-((R)-2-hydroxy-propylamino)-2-methylsulfanyl-pyrimidine-5-carbaldehyde (17.7 g, 78 mmol) and (2,4-difluorophenoxy)acetic acid methyl ester (31.6 g, 156 mmol) in anhydrous dimethyl formamide (300 mL) was added potassium carbonate (30 g, 218 mmol). The reaction mixture was heated to 60° C. and after 18 hours, reaction mixture was cooled and DMF was distilled off. Residue suspended in water (300 mL) and extracted with dichloromethane, washed with brine and dried over magnesium sulfate. Filtered and concentrated under vacuum to give 29.5 g crude material which was chromatographed on silica gel column eluding with 1% methanol in dichloromethane to give 17.5 g 6-(2,4-difluorophenoxy)-8-((R)-2-hydroxypropyl)-2-methylsulfanyl-8H-pyrido[2,3-d]pyrimidin-7-one (mass spec M+1=274).

Step B: Preparation of 6-(2,4-Difluorophenoxy)-8-((R)-2-hydroxypropyl)-2-methanesulfonyl-8H-pyrido[2,3-d]pryimidin-7-one

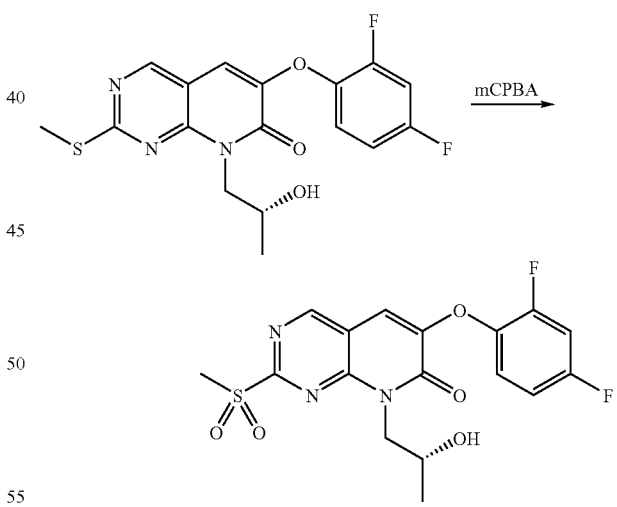

To a dichloromethane (200 mL) solution of 6-(2,4-difluorophenoxy)-8-((R)-2-hydroxypropyl)-2-methylsulfanyl-8H-pyrido[2,3-d]pyrimidin-7-one (9.38 g, 24.7 mmol) at 5° C. was added portion wise m-chloroperbenzoic (12.5 g, 54 mmol) acid and stirred for 24 hours. Reaction mixture washed with aqueous sodium sulfite, aqueous sodium bicarbonate and dried over magnesium sulfate. Filtered and evaporated to give 10.7 g 6-(2,4-difluorophenoxy)-8-((R)-2-hydroxypropyl)-2-methanesulfonyl-8H-pyrido[2,3-d]pyrimidin-7-one (mass spec M+1=412).

Step C: Preparation of 6-(2,4-Difluoro-phenoxy)-2-((S)-2-hydroxy-1-methyl-ethylamino)-8-((R)-2-hydroxy-propyl)-8H-pyrido[2,3-d]pyrimidin-7-one

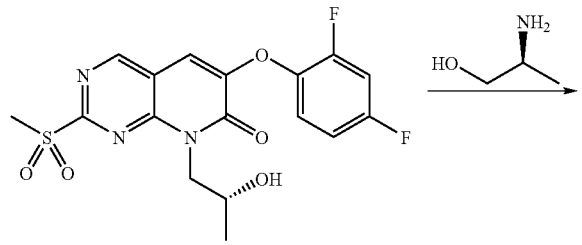

To a THF (5 mL) solution of 6-(2,4-difluorophenoxy)-8-((R)-2-hydroxypropyl)-2-methanesulfonyl-8H-pyrido[2,3-d]pyrimidin-7-one (615 mg, 1.5 mmol) was added (S)-2-amino-1-propanol (1.2 mL, 15 mmol) and stirred overnight at RT. Concentrated under vacuum and chromatographed on silica gel eluding with 2% methanol in dichloromethane and converted to the hydrochloride salt to give 295 mg 6-(2,4-difluoro-phenoxy)-2-((S)-2-hydroxy-1-methyl-ethylamino)-8-((R)-2-hydroxy-propyl)-8H-pyrido[2,3-d]pyrimidin-7-one (mass spec. M+1=407, MP=186.0-189.1° C.).

Example 5

Preparation of 6-(2,4-Difluoro-phenoxy)-2-(R)-2-hydroxy-1-methyl-ethylamino)-8-((R)-2-hydroxy-propyl)-8H-pyrido[2,3-d]pyrimidin-7-one

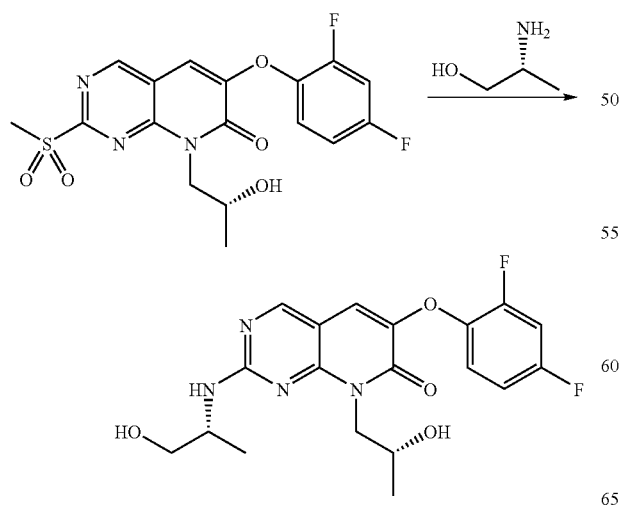

To a tetrahydrofuran (5 mL) solution of 6-(2,4-difluorophenoxy)-8-((R)-2-hydroxypropyl)-2-methanesulfonyl-8H-pyrido[2,3-d]pyrimidin-7-one (400 mg, 1 mmol) was added (R)-2-amino-1-propanol (0.38 mL, 5 mmol) and stirred overnight at room temperature. Concentrated under vacuum and chromatographed on silica gel eluding with 2% methanol in dichloromethane and converted to the hydrochloride salt to give 350 mg 6-(2,4-difluoro-phenoxy)-2-((R)-2-hydroxy-1-methyl-ethylamino)-8-((R)-2-hydroxy-propyl)-8H-pyrido[2,3-d]pyrimidin-7-one (mass spec. M+1=407, MP=181.5-184.4° C.).

Example 6

Preparation of 6-(2,4-Difluorophenoxy)-2-(2-hydroxy-1,1-dimethyl-ethylamino)-8-((R)-2-hydroxypropyl)-8H-pyrido[2,3-d]pyrimidin-7-one

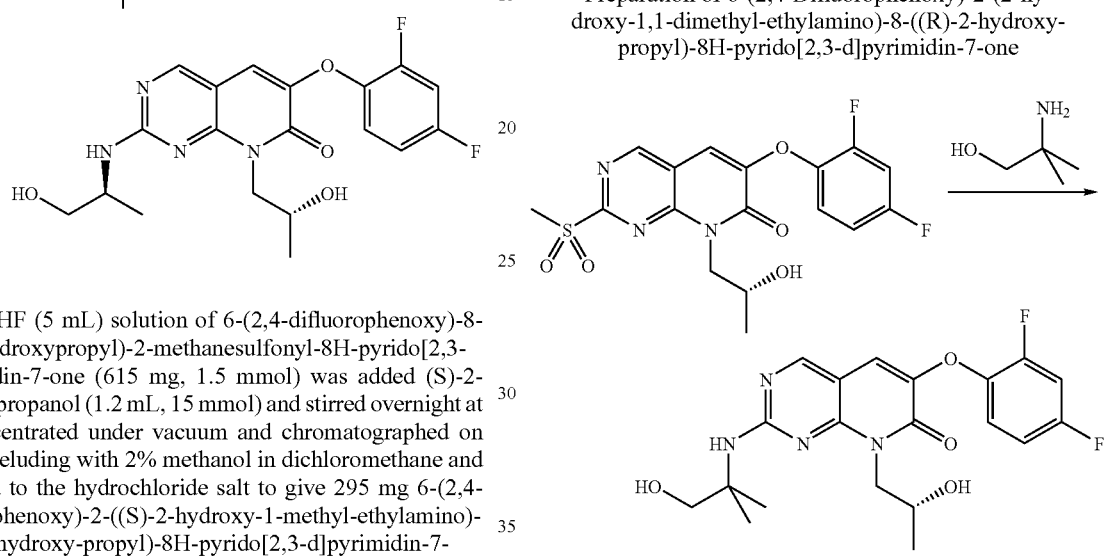

A mixture of 6-(2,4-difluorophenoxy)-8-((R)-2-hydroxypropyl)-2-methanesulfonyl-8H-pyrido[2,3-d]pyrimidin-7-one (886 mg, 2.15 mmol) and 2-amino-2-methyl-1-propanol (5.15 g, 58 mmol) was heated at 60° C. under nitrogen for 2 hours. Cooled and chromatographed on silica gel eluding with 2% methanol in dichloromethane to give after converting to hydrochloride salt 385 mg 6-(2,4-Difluorophenoxy)-2-(2-hydroxy-1,1-dimethyl-ethylamino)-8-((R)-2-hydroxypropyl)-8H-pyrido[2,3-d]pyrimidin-7-one (mass spec. M+1=421, MP=182.0-183.9° C.).

Example 7

Preparation of 6-(2,4-Difluoro-phenoxy)-2-((S)-2-hydroxy-1-methyl-ethylamino)-8-(2-oxopropyl)-8H-pyrido[2,3-d]pyrimidin-7-one

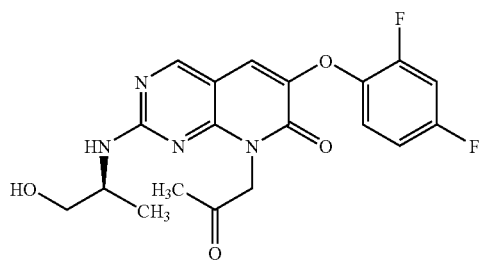

Step A: Preparation of 6-(2,4-Difluorophenoxy)-2-methanesulfonyl-8-(2-oxopropyl)-8H-pyrido[2,3-d]pyrimidin-7-one

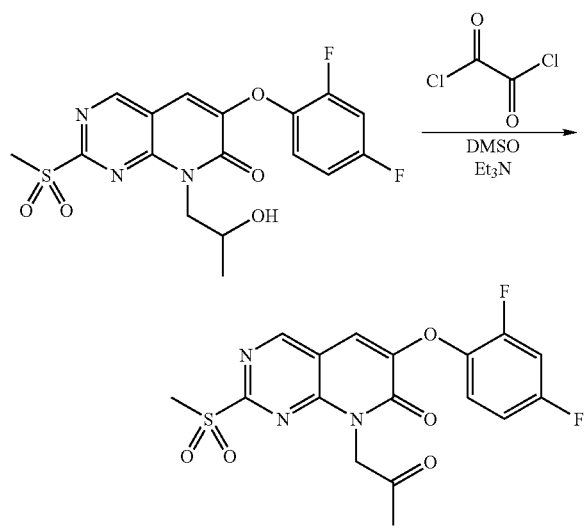

To a dichloromethane (100 mL) solution of oxalyl chloride (1.05 mL, 12 mmol) at −60° C. was added dimethyl sulfoxide (1.7 mL, 24 mmol) and 6-(2,4-difluorophenoxy)-8-(2-hydroxypropyl)-2-methanesulfonyl-8H-pyrido[2,3-d]pyrimidin-7-one (4.12 g, 10 mmol). To this mixture was added triethylamine (7 mL, 50 mmol) and stirred overnight. Added water (100 mL) and extracted with dichloromethane, washed with brine and dried over magnesium sulfate. Filter and concentrated under vacuum, chromatographed on silica gel eluding with 2% methanol in dichloromethane to give 1.0 g 6-(2,4-fluorophenoxy)-2-methanesulfonyl-8-(2-oxopropyl)-8H-pyrido[2,3-d]pyrimidin-7-one (mass Spec. M+1=410)

Step B: Preparation of 6-(2,4-Difluorophenoxy)-2-((S)-2-hydroxy-1-methyl-ethylamino)-8-(2-oxopropyl)-8H-pyrido[2,3-d]pyrimidin-7-one

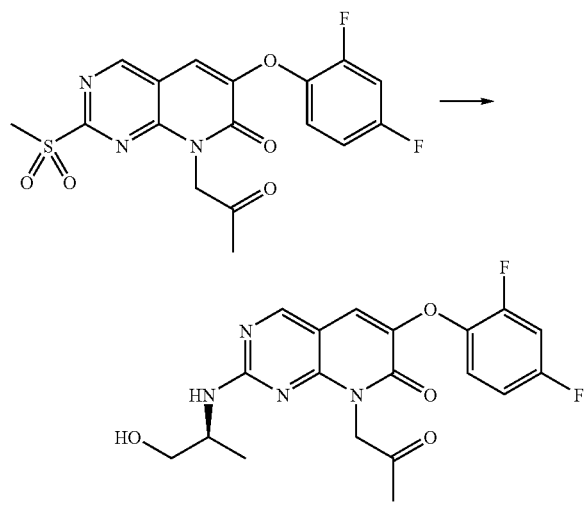

To a THF suspension of 6-(2,4-difluorophenoxy)-2-methanesulfonyl-8-(2-oxopropyl)-8H-pyrido[2,3-d]pyrimidin-7-one (412 mg, 1 mmol) was added (S)-2-amino-1-propanol (0.39 mL, 5 mmol) at RT and stirred overnight. Concentrated under vacuum and chromatographed on silica gel eluding with 2% methanol in dichloromethane to give after conversion to the hydrochloride salt 330 mg 6-(2,4-Difluorophenoxy)-2-((S)-2-hydroxy-1-methyl-ethylamino)-8-(2-oxopropyl)-8H-pyrido[2,3-d]pyrimidin-7-one (Mass spec. M+1=405, MP=207.9-214.6° C.).

Example 8

Preparation of 6-(2,4-Difluorophenoxy)-2-((R)-2-hydroxy-1-methyl-ethylamino)-8-(2-oxopropyl)-8H-pyrido[2,3-d]pyrimidin-7-one

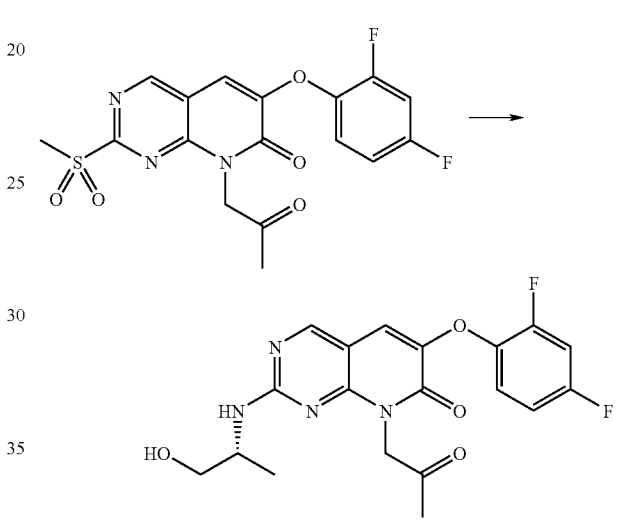

To a tetrahydrofuran (10 mL) suspension of 6-(2,4-difluorophenoxy)-2-methanesulfonyl-8-(2-oxopropyl)-8H-pyrido[2,3-d]pyrimidin-7-one (417 mg, 1 mmol) was added (R)-(−)-2-amino-1-propanol (0.40 mL, 5 mmol) at room temperature and stirred overnight. Concentrated under vacuum and chromatographed on silica gel eluding with 2% methanol in dichloromethane to give after conversion to the hydrochloride salt 330 mg 6-(2,4-Difluorophenoxy)-2-((R)-2-hydroxy-1-methyl-ethylamino)-8-(2-oxopropyl)-8H-pyrido[2,3-d]pyrimidin-7-one (Mass spec. M+1=405, MP=207.8-216.4° C.).

Example 9

In Vitro Assay

This example illustrates a p38 (MAP) kinase in vitro assay useful for evaluating the compounds of the present invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and $\gamma$-$^{33}$P-ATP. After incubating for an additional 20 min at 30° C., the reaction was terminated by adding 0.75% phosphoric acid. The phosphorylated MBP was then separated from the residual $\gamma$-$^{33}$P-ATP using a phosphocellulose membrane (Millipore, Bedford, Mass.) and quantitated using a scintillation counter (Packard, Meriden, Conn.).

Using the above assay, compounds of the invention were shown to be inhibitors of p38 MAP kinase. The compounds of the invention exhibited p38 $IC_{50}$ values in the range of from less than 0.001 to 0.1 μM. For example, 6-(2,4-difluorophenoxy)-8-(3-hydroxy-propyl)-2-(tetrahydro-pyran-4-ylamino)-8H-pyrido[2,3-d]pyrimidin-7-one showed an $IC_{50}$ of 0.0008 μM using the above assay.

Example 10

In Vitro Assay

This example illustrates a human whole blood (HWB) in vitro assay (i.e LPS-induced IL-1β production in undiluted human whole blood via inhibition of p38 MAP kinase) for evaluating the compounds of the present invention and the comparative results of corresponding alkyl analogs.

LPS (lipopolysaccharide) treatment of human whole blood induces IL-1β (Interleukin-1β) production that can be measured by an IL-1β specific ELISA. Human whole blood was pre-incubated with the indicated concentrations of a compound of the present invention in 0.5% DMSO (final concentration) for 30 min at 37° C. Samples were stimulated with 0.5 μg/mL of lipopolysaccharide (LPS, from Sigma) (final concentration) for 18 hours to induce the synthesis and secretion of IL-1β which was measured using an IL-1β ELISA.

Solution Preparation

Compound Solutions

A stock solution of 6 mM in DMSO (from Sigma) was prepared by dissolving the compound in DMSO in 449 μL of DMSO. From the 6 mM stock solution, six subsequent half-log serial dilutions in DMSO were performed to give the following concentrations: 1.9 mM, 600, 190, 60, 19, and 6 μM. Label tubes 1-7. The 6 mM stock solution in tube 1. 216 μL DMSO was placed in each of tubes 2-7. From tube 1,100 μL was transferred to tube 2. Tube 2 was vortexed and 100 μL was transferred from tube 2 to tube 3. This process was repeated to tube 7.

Using the serial dilutions of the compound in DMSO prepared above, an additional dilution 1/20 (10 μL into 190 μL RPMI 1640 medium, from Gibco-BRL) was performed to give a final compound concentration curve of 30, 10, 2.9, 1, 0.3, 0.1, 0.03 μM.

LPS Solutions

Reconstitution of LPS: in the 10 mg. vial of LPS, 10 mL 1× Phosphate-Buffered Saline (i.e., 1×PBS, from Gibco-BRL) was added, mixed well and transferred to a 50 mL tube. Another 10 mL was added to the LPS vial, followed by rinsing, and this rinse was added to the 50 mL tube and mixed will. The solution was filtered and sterilized, and aliquotted in desired amounts (100 μL aliquot was sufficient for 4 plates). This yielded a 0.5 mg/mL stock which was diluted 1/100 for use in protocol. Just prior to use, the LPS stock was diluted 1/100 (100 μL in 10 mL of RPMI)

Assay Procedure

The Assay was performed in a 96 well U bottom plate (from Costar). Two controls were included in each assay, plus and minus LPS in the absence of compound. All samples and controls were performed in triplicate.

Human blood (from donors who had received no medication for at least 14 days, no alcohol for 48 hours) was collected into siliconized vacutainers containing heparin (19 units/ml). A 25 μL aliquot of 5% DMSO in RPMI 1640 was added to control wells (plus and minus LPS controls). 25 mL aliquots of each compound concentration prepared above were dispensed to designated wells. 200 μL of human whole blood was added to each well and incubated at 37° C. and 5% $CO_2$ for 30 minutes. 25 μL of diluted LPS was dispensed to all wells except minus LPS control wells. 25 μL of RPMI was added to minus LPS control wells.

The plates were incubated at 37° C. and 5% $CO_2$ for 18 hours. After incubation, plates were centrifuged at 400×g to pellet cells and collect plasma, taking care not to disturb the pellet. The plasma was transferred to a new 96 well polypropylene plate. ELISA was performed immediately and remaining plasma was stored at −20° C., in case needed for re-testing.

ELISA Protocol

The IL-1β ELISA used two anti-IL-1β monoclonal antibodies: ILβ1-H6 (1 mg/mL) and ILβ1-H67 (2.71 mg/mL).

Materials

Recombinant human IL-1β (rhuIL-1β, 2.5 μg/mL) was obtained from R&D Systems.

Phosphate-Buffered Saline-Dulbecco's (1×PBS) was obtained from Gibco-BRL.

Phosphate-Buffered Saline (10×PBS) was obtained from Gibco-BRL.

Dulbeccos' modification without calcium and magnesium, pH 7.2.

Unopened bottles were stored at Room Temperature.

ELISA Incubation Buffer (EIB)

0.1% BSA/PBS 1 g Bovine serum albumin (BSA)

100 mL of 10×PBS

Add deionized water to 1 liter and store at 4° C.

ELISA Wash Buffer (EWB)

0.05% Tween/PBS 0.5 mL Tween 20

100 mL 10×PBS

Add deionized water to 1 liter and store at 4° C.

Blocking Buffer—3% Nonfat-dry milk/PBS 15 g nonfat-dry milk powder (Carnation)

50 mL 10×PBS

Add distilled water to 500 mL and store at 4° C.

Peroxidase Conjugated Streptavidin (from Pharmingen)

Dilute approximately 1:3000 (10 μL/30 mL) in EWB buffer.

0.1 M Citrate Buffer, pH 4.5
9.6 g. citric acid (MW 192.1, from Sigma)
14.7 g. tri-sodium citrate (MW 294.1, from Sigma)
Adjust to pH 4.5 using NaOH and add distilled water to 500 mL. Store at 4° C.
OPD Substrate solution
1 mg/mL OPD/0.03% $H_2O_2$/citrate buffer
1 tablet o-phenylenediamine (OPD, from Zymed)
12 μL of 30% hydrogen peroxide
12 mL of 0.1 M citrate buffer Preparation of Standards (Prepare Fresh Just Prior to Placing on Plate).

A stock solution of rhuIL-1β (2.5 μg/mL) was used to construct a standard curve. The concentrations for the curve are: 12500, 4167, 1389, 463, 154, 51 and 17 pg/mL. Tubes were labeled 1-8. rhuIL-1β stock solution was diluted 1/500 (3 μL of stock+597 μL of EWB) in tube 1. 400 μL EWB was dispensed in tubes 2-8. From tube 1, 200 μL was transferred to tube 2 and vortexed. 200 μL was transferred from tube 2 to tube 3. Repeat this process to tube 7. Tube 8 was used as the ELISA assay blank.

Plasma samples were diluted 1:4 in EWB (20 μL of plasma+60 μL of EWB).

Preparation of Antibody Solutions.

Antibody ILβ1-H6 was diluted 1/100 in 1×PBS to generate 10 μg/mL solution. Per plate, 50 μL of antibody was diluted in 5 mL PBS. Antibody ILβ1-H67 was diluted 1/100 in EWB to generate 2 μg/mL solution. Per plate, 3.69 μL of antibody was diluted in 5 mL EIB.

Procedure 96-well EIA plates were coated with 50 μL per well of antibody ILβ1-H6 (10 μg/mL), shaken gently to clear any air bubbles, and sealed with plate sealer and incubate in a humidified chamber overnight at 4° C. The plates were emptied and tapped dry on a lint free paper towel. Non-specific binding sites were blocked with 175 μL per well of Blocking Buffer for 1-2 hours at room temperature. The plates were washed once with EWB (i.e., empty plate, filled with 150 μL EWB, emptied and tapped dry on a lint free paper towel).

Triplicate 25 μL aliquots of standard were added to appropriate wells. (Each plate has its own standard curve.). A 25 μL aliquot of diluted plasma was added to the appropriate well. To all wells, 25 μL of biotinylated monoclonal antibody ILβ1-H67 (2 μg/mL) was added. The plates were sealed with plate sealer and incubated for 2 hours at room temperature (or overnight at 4° C.) while gently shaking (Bellco Mini-Orbital Shaker, setting 3.5). After incubation, plates were washed 3× with EWB (as described above). A 50 μL aliquot of peroxidase-streptavidin, diluted 1:3000 in EIB, was added to each well. Plates were sealed with plate sealer, incubated plates for 1 hour at room temperature while shaking, and washed 3× as described above.

An OPD tablet was dissolved in citrate buffer, (1 tablet/12 mL citrate buffer), and 12 μL of 30% $H_2O_2$ was added to OPD/citrate buffer). 50 μL of OPD substrate solution was dispensed to each well, and plates were incubated in the dark for 30 minutes at room temperature for color development. Plates were read at dual wavelength: Sample filter=450 nm/Reference filter=650 nm. The values from the samples containing the standard were used to graph a standard curve (absorbance vs. concentration) used to determine concentrations of unknown samples.

Statistical Method

If the concentration-inhibition curve does not include points on either side of 50%, then the $IC_{50}$ was reported as >highest concentration or <lowest concentration. Otherwise, if the number of concentration was ≧5, the data was fitted to the following 2-parameter model to estimate an $IC_{50}$:

$$\text{Mean \% Inhibition} = \frac{100}{1 + \left(\frac{IC_{50}}{Conc}\right)^n}$$

This model assumes the minimum and maximum response were 0% and 100%, respectively, and estimates the $IC_{50}$ and the slope parameter. If the nonlinear regression fails or if the number of concentrations tested was <5, linear regression was used to estimate the $IC_{50}$ using the 2 points that flank 50%.

If linear regression was used to estimate the $IC_{50}$, this was output in the assay notes, and can also be seen with the presence (nonlinear regression) or absence (linear regression) of the $IC_{50}$ standard error and the slope parameter.

Results

Using the above assay, compounds of the invention were shown to inhibit LPS-induced IL-1β production in undiluted human whole blood via inhibition of p38 MAP kinase, which mediates IL-1β production as noted above. Compounds of the invention exhibited $IC_{50}$ values for LPS-induced IL-1β production in undiluted human whole blood in the range of from <0.001 μM to 0.30 μM. For example, 6-(2,4-difluoro-phenoxy)-8-((R)-2-hydroxy-propyl)-2-(tetrahydro-pyran-4-ylamino)-8H-pyrido[2,3-d]pyrimidin-7-one showed an $IC_{50}$ of 0.001 μM.

Surprisingly, the inhibition of LPS-induced IL-1β production using compounds of the invention wherein $R^2$ of formula (I) is hydroxyalkyl or alkoxyalkyl, is substantially greater than results from corresponding compounds wherein $R^2$ is methyl or other alkyl. This unexpected advantage of the invention is illustrated more fully in Table 2, in which representative compounds of the invention where $R^2$ (of formula I) is hydroxyalkyl are compared to the corresponding analogs where $R^2$ is methyl). Compounds in the first or leftmost column of Table 1 are prepared as described in the examples herein, and are also shown in Table 1. Compounds in the second or center column of Table 2 were prepared according to the procedures reported in WO 02/064594. The values in the third or right-most column correspond to the ratio:

($IC_{50}$ inhibition of IL-1β production where $R^2$=hydroxyalkyl)/($IC_{50}$ inhibition of IL-1β production where $R^2$=methyl).

As can be seen from Table 2, compounds wherein $R^2$ is hydroxyalkyl provide inhibition of LPS-induced IL-1β production in undiluted human whole blood that is on the order of 2.7 to >100 times, i.e., 270% to >10,000%, greater than the corresponding methyl analogs (12=methyl).

TABLE 2

| R² = hydroxyalkyl | R² = alkyl (methyl) | IC₅₀/IC₅₀ ratio |
|---|---|---|
| (structure) | (structure) HCl | 43.4 |
| (structure) | (structure) HCl | 27.8 |
| (structure) | (structure) HCl | 9.9 |
| (structure) HCl | (structure) | 100 |
| (structure) HCl | (structure) HCl | 17.9 |

TABLE 2-continued
| R² = hydroxyalkyl | R² = alkyl (methyl) | IC₅₀/IC₅₀ ratio |
|---|---|---|
| 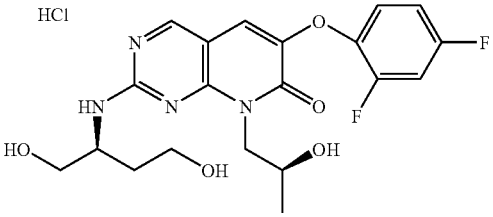 | 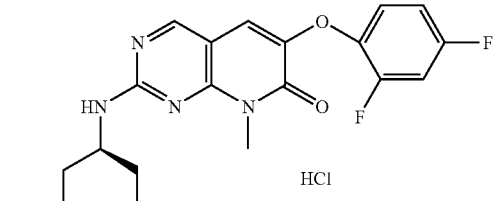 | 5.3 |
| 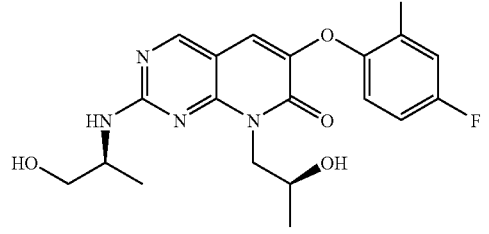 | 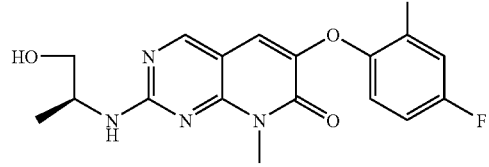 | 17.4 |
| 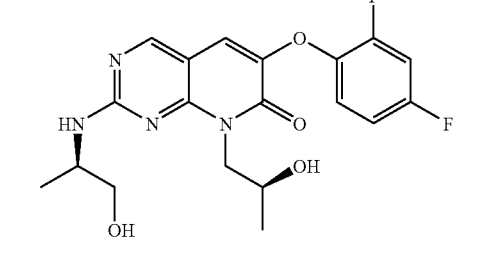 | 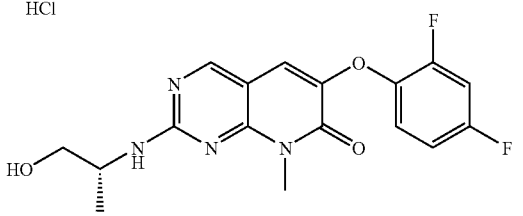 | 24.6 |
| 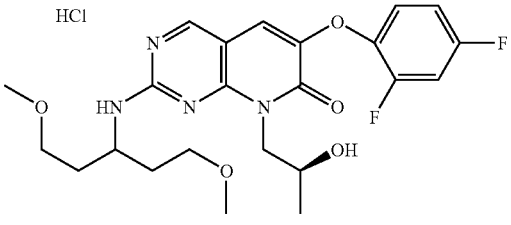 | 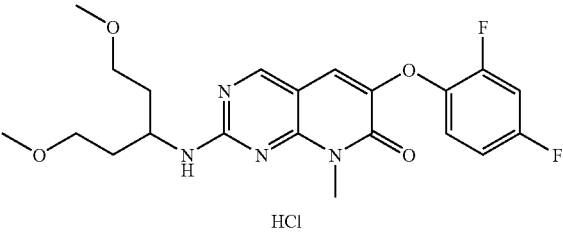 | 2.7 |
| 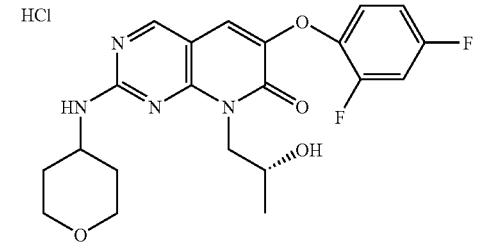 | 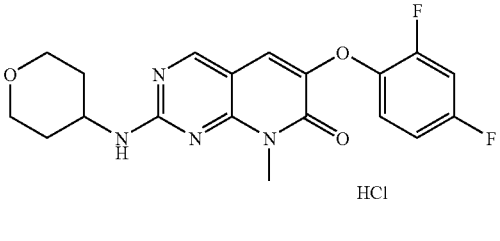 | 200 |

TABLE 2-continued
| R² = hydroxyalkyl | R² = alkyl (methyl) | IC₅₀/IC₅₀ ratio |
|---|---|---|
| 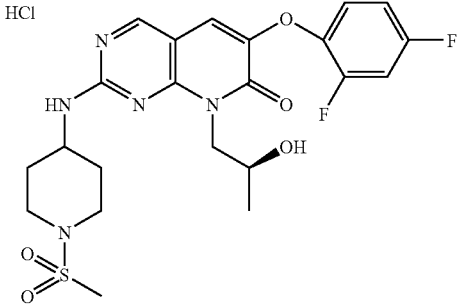 | 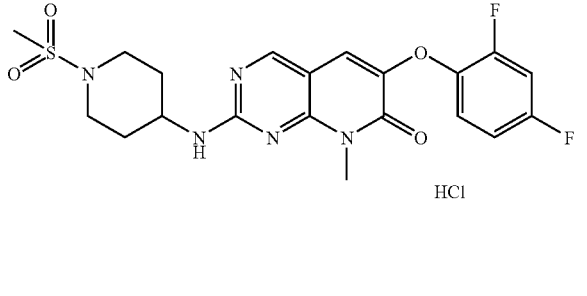 | 7.3 |
| 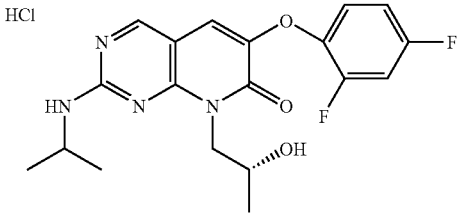 | 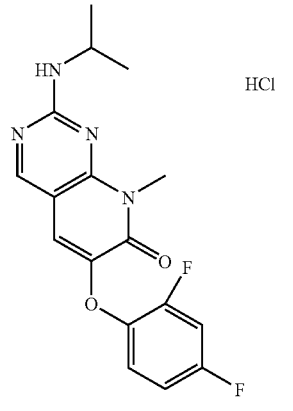 | 11.4 |
| 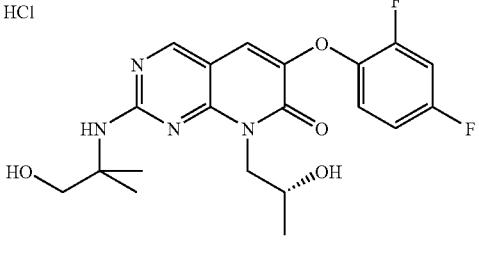 | 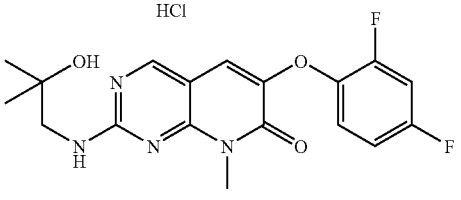 | 4.7 |
| 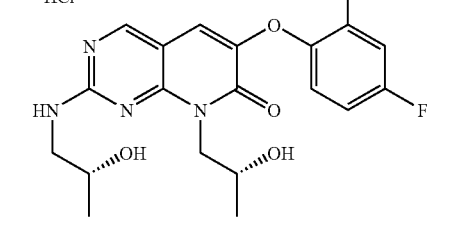 | 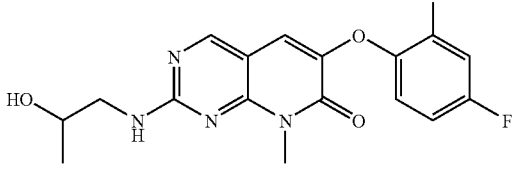 | 3.9 |
| 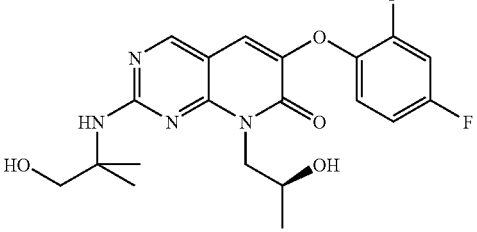 | 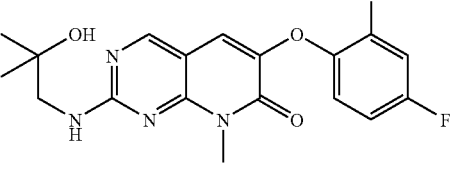 | 6.2 |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A compound of the formula:

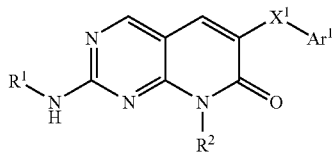

wherein
$X^1$ is O, $S(O)_n$, or C=O;
wherein
n is 0, 1 or 2;
$Ar^1$ is aryl or heteroaryl;
$R^1$ is hydroxyalkyl; and
$R^2$ is oxoalkyl.

2. The compound of claim 1, wherein $Ar^1$ is aryl.
3. The compound of claim 1, wherein $Ar^1$ is heteroaryl.
4. The compound of claim 2, wherein $X^1$ is O.
5. The compound of claim 4, wherein:
$R^1$ is (R)-2-hydroxy-1-methylethyl or (S)-2-hydroxy-1-methylethyl.

6. A compound of the formula:

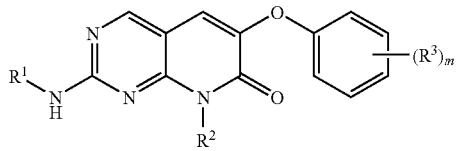

wherein:
m is from 0 to 4;
$R^1$ is hydroxyalkyl;
$R^2$ is oxoalkyl; and
each $R^3$ independently is: alkyl; alkoxy; halo; or haloalkyl.

7. The compound of claim 6, wherein $R^3$ is halo.
8. The compound of claim 6, wherein m is from 0 to 2.
9. The compound of claim 6, wherein n is 2 and $R^3$ is halo.
10. The compound of claim 1, wherein said compound is selected from:
6-(2,4-Difluoro-phenoxy)-2-((S)-2-hydroxy-1-methyl-ethylamino)-8-(2-oxo-propyl) -8H-pyrido[2,3 -d]pyrimidin-7-one; and
6-(2,4-Difluoro-phenoxy)-2-((R)-2-hydroxy-1-methyl-ethylamino)-8-(2-oxo-propyl) -8H-pyrido [2,3 -d]pyrimidin-7-one.

11. A composition comprising:
(a) a pharmaceutically acceptable excipient; and
(b) a compound of claim 1.

12. A compound of the formula:

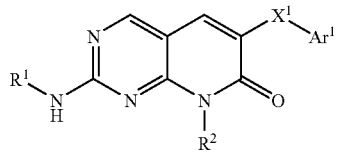

wherein
$X^1$ is O, $S(O)_n$, or C=O;
wherein
n is 0, 1 or 2;
$Ar^1$ is phenyl optionally substituted one or more times with alkyl, halo, haloalkyl or alkoxy;
$R^1$ is hydroxyalkyl; and
$R^2$ is oxoalkyl.

13. The compound of claim 12, wherein $X^1$ is O.
14. The compound of claim 13, wherein $Ar^1$ is 2,4-disubstituted phenyl.
15. The compound of claim 14, wherein $Ar^1$ is 2,4-halophenyl.
16. The compound of claim 15, wherein $Ar^1$ is 2,4-difluorophenyl.
17. The compound of claim 16, wherein:
$R^1$ is (R)-2-hydroxy-1-methylethyl or (S)-2-hydroxy-1-methylethyl.

* * * * *